US009392975B2

(12) United States Patent  
McGonigle et al.

(10) Patent No.: US 9,392,975 B2  
(45) Date of Patent: *Jul. 19, 2016

(54) CONSISTENT SIGNAL SELECTION BY SIGNAL SEGMENT SELECTION TECHNIQUES

(71) Applicant: Nellcor Puritan Bennett Ireland, Mervue, Galway (IE)

(72) Inventors: Scott McGonigle, Edinburgh (GB); Paul S. Addison, Edinburgh (GB); James N. Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 37 days.

This patent is subject to a terminal disclaimer.

(21) Appl. No.: 14/020,547

(22) Filed: Sep. 6, 2013

(65) Prior Publication Data  
US 2014/0012109 A1 Jan. 9, 2014

Related U.S. Application Data

(63) Continuation of application No. 12/437,326, filed on May 7, 2009, now Pat. No. 8,532,932.

(60) Provisional application No. 61/077,062, filed on Jun. 30, 2008, provisional application No. 61/077,130, filed on Jun. 30, 2008.

(51) Int. Cl.  
*A61B 1/00* (2006.01)  
*A61B 5/00* (2006.01)  
*A61B 5/1455* (2006.01)  
*G06K 9/00* (2006.01)  
*A61B 5/024* (2006.01)

(52) U.S. Cl.  
CPC ............ *A61B 5/7221* (2013.01); *A61B 5/02416* (2013.01); *A61B 5/14551* (2013.01); *A61B 5/726* (2013.01); *G06K 9/0053* (2013.01); *A61B 5/7203* (2013.01); *A61B 5/7207* (2013.01)

(58) Field of Classification Search  
CPC ............. A61B 5/02416; A61B 5/7278; A61B 5/7203; A61B 5/02108; G06F 17/14  
See application file for complete search history.

(56) References Cited

U.S. PATENT DOCUMENTS

| | | | |
|---|---|---|---|
| 4,800,495 A | 1/1989 | Smith | |
| 5,218,962 A | 6/1993 | Mannheimer et al. | |
| 5,381,803 A | 1/1995 | Herleikson et al. | |
| 5,482,036 A | 1/1996 | Diab et al. | |
| 5,490,505 A | 2/1996 | Diab et al. | |
| 5,517,988 A | 5/1996 | Gerhard | |
| 5,558,096 A | 9/1996 | Palatnik | |
| 5,595,176 A | 1/1997 | Yamaura | |
| 5,632,272 A | 5/1997 | Diab et al. | |
| 5,685,299 A | 11/1997 | Diab et al. | |
| 5,713,355 A | 2/1998 | Richardson et al. | |
| 5,769,785 A | 6/1998 | Diab et al. | |
| 6,002,952 A | 12/1999 | Diab et al. | |
| 6,036,642 A | 3/2000 | Diab et al. | |
| 6,067,462 A | 5/2000 | Diab et al. | |
| 6,081,735 A | 6/2000 | Diab et al. | |
| 6,206,830 B1 | 3/2001 | Diab et al. | |
| 6,263,222 B1 | 7/2001 | Diab et al. | |
| 6,501,975 B2 | 12/2002 | Diab et al. | |
| 6,519,486 B1 | 2/2003 | Edgar, Jr. et al. | |
| 6,631,281 B1 | 10/2003 | Kastle | |
| 6,654,623 B1 | 11/2003 | Kastle | |
| 6,654,624 B2 | 11/2003 | Diab et al. | |
| 6,684,090 B2 | 1/2004 | Ali et al. | |
| RE38,476 E | 3/2004 | Diab et al. | |
| 6,699,194 B1 | 3/2004 | Diab et al. | |
| RE38,492 E | 4/2004 | Diab et al. | |
| 6,805,673 B2 | 10/2004 | Dekker | |

(Continued)

FOREIGN PATENT DOCUMENTS

| | | |
|---|---|---|
| EP | 0429025 A2 | 5/1991 |
| EP | 0801960 A2 | 10/1997 |
| WO | WO 00/21438 | 4/2000 |

OTHER PUBLICATIONS

Dyck, W. and Collette, M.: "A microcontroller-based device for monitoring blood pressure in the field", Defence Research Establishment Ottawa, Technical Note, vol. 93, No. 29, Jun. 1994, XP002609850, *abstract: figures 4,5, p. 16, line 19—p. 17, line 4.

PCT International Search Report, International Application No. PCT/IB2009/006182, Applicant: Nellcor Puritan Bennett Ireland, Date of Mailing: Dec. 21, 2010, International Filing Date: Jun. 29, 2009.

Addison, Paul S., The Illustrated Wavelet Transform Handbook, Taylor & Francis Group, 2002.

Primary Examiner — Mary Zeman

(74) Attorney, Agent, or Firm — Shvarts & Leiz LLP

(57) ABSTRACT

According to embodiments, techniques for selecting a consistent part of a signal, including a photoplethysmograph (PPG) signal, are disclosed. A pulse oximetry system including a sensor or probe may be used to obtain a PPG signal from a subject. Signal peaks may be identified in the PPG signal. Characteristics of the signal peaks, including the amplitude levels of the signal peaks and/or the time-distance between the signal peaks may be used to determine if the PPG signal is consistent. In an embodiment, signal peaks are processed based on a consistency metric, and the processed signal peaks are compared to the consistency metric to determine if the PPG signal is consistent. If the PPG signal is determined to be consistent, the PPG signal may be further analyzed to determine an underlying signal parameter, including, for example, a patient respiration rate. If the PPG signal is determined to be inconsistent, the inconsistent portion of the signal may be removed from the overall signal or otherwise transformed.

18 Claims, 16 Drawing Sheets

(56) References Cited

U.S. PATENT DOCUMENTS

| | | |
|---|---|---|
| 6,810,277 B2 | 10/2004 | Edgar, Jr. et al. |
| 6,811,538 B2 | 11/2004 | Westbrook et al. |
| 6,816,741 B2 | 11/2004 | Diab |
| 6,822,564 B2 | 11/2004 | Al-Ali |
| 6,826,419 B2 | 11/2004 | Diab et al. |
| 6,839,659 B2 | 1/2005 | Tarassenko et al. |
| 6,852,083 B2 | 2/2005 | Caro et al. |
| 6,996,427 B2 | 2/2006 | Ali et al. |
| 7,006,856 B2 | 2/2006 | Baker, Jr. et al. |
| 7,020,507 B2 | 3/2006 | Scharf et al. |
| 7,072,702 B2 | 7/2006 | Edgar, Jr. et al. |
| 7,139,599 B2 | 11/2006 | Terry |
| 7,162,288 B2 | 1/2007 | Nordstrom et al. |
| 7,248,910 B2 | 7/2007 | Li et al. |
| 7,355,512 B1 | 4/2008 | Al-Ali |
| 7,367,339 B2 | 5/2008 | Hickle |
| 7,381,188 B1 | 6/2008 | Farazi |
| 7,407,485 B2 | 8/2008 | Huiku |
| 7,460,899 B2 | 12/2008 | Almen |
| 7,499,740 B2 | 3/2009 | Nordstrom et al. |
| 7,582,061 B2 | 9/2009 | Li et al. |
| 8,478,538 B2 | 7/2013 | McGonigle et al. |
| 8,532,932 B2 * | 9/2013 | McGonigle et al. ............ 702/19 |
| 2003/0036685 A1 | 2/2003 | Goodman |
| 2005/0004479 A1 | 1/2005 | Townsend et al. |
| 2005/0197579 A1 | 9/2005 | Baker, Jr. |
| 2006/0135860 A1 | 6/2006 | Baker, Jr. et al. |
| 2006/0137577 A1 | 6/2006 | Chang et al. |
| 2006/0195025 A1 | 8/2006 | Ali et al. |
| 2006/0241708 A1 | 10/2006 | Boute |
| 2006/0258921 A1 | 11/2006 | Addison et al. |
| 2006/0258927 A1 | 11/2006 | Edgar, Jr. et al. |
| 2007/0238937 A1 | 10/2007 | Chang et al. |
| 2008/0262326 A1 | 10/2008 | Hete et al. |
| 2009/0326351 A1 | 12/2009 | Addison et al. |
| 2009/0326395 A1 | 12/2009 | Watson |
| 2009/0326831 A1 | 12/2009 | McGonigle et al. |

\* cited by examiner

CONSISTENT SIGNAL SELECTION BY SIGNAL SEGMENT SELECTION TECHNIQUES

CROSS REFERENCE TO RELATED APPLICATION

This application is a continuation of U.S. patent application Ser. No. 12/437,326, filed on May 7, 2009, which claims priority to U.S. Provisional Application No. 61/077,062, filed Jun. 30, 2008, and U.S. Provisional Application No. 61/077,130, filed Jun. 30, 2008, all of which are incorporated herein by reference in their entireties.

SUMMARY

The present disclosure is related to signal processing systems and methods, and more particularly, to systems and methods for selecting a consistent portion of a signal for parameter identification.

In an embodiment, a signal may be obtained, and a portion of the obtained signal may be analyzed for consistency. Signal extrema (e.g., local maxima and/or minima in the signal amplitude versus time) may be identified, and characteristics of the signal extrema may be analyzed to determine signal consistency. In an embodiment, signal peaks (local maxima in the signal amplitude versus time) may be identified and processed based on a consistency metric. The processed signal peaks may then be compared to the consistency metric, and the most consistent portion of the obtained signal (or a sufficiently consistent part of the obtained signal) may be identified in this way. In an embodiment, a consistent portion of a signal is found and used to determine an underlying parameter from the obtained signal. For example, a consistent portion of the signal may be used to determine a respiration rate of a patient.

For the purposes of illustration, and not by way of limitation, in an embodiment disclosed herein the obtained signal is a photoplethysmograph (PPG) signal drawn from any suitable source, such as a pulse oximeter. The obtained signal may be filtered, processed or otherwise transformed before the techniques described herein are applied to the signal. For example, the PPG signal may first be transformed by detecting and processing the up and down strokes of a preliminary PPG signal to produce the obtained PPG signal. Further, transformation of the preliminary PPG signal into the obtained PPG signal may include low-pass filtering, removal of noise-components, and/or interpolation methods to remove various undesirable artifacts that may be present in the preliminary PPG signal.

In an embodiment, a consistent portion of a (obtained) PPG signal may be determined by identifying the amplitude levels of one or more signal peaks. For example, a signal peak may be identified and lower and an upper thresholds may be set relative to the amplitude level of the signal peak. In an embodiment, a lower threshold may be set at an amplitude level smaller than the amplitude level of the PPG signal peak, and an upper threshold may be set at an amplitude level larger than the amplitude level of the PPG signal peak. An amplitude level of a second PPG signal peak may be identified, and a computer or process may then determine if the amplitude level of the second PPG signal peak is larger than the lower threshold amplitude level and smaller than the upper threshold amplitude level. If the amplitude level of the second PPG signal peak is larger than the lower threshold amplitude level and smaller than the upper threshold amplitude level, then the corresponding portion of the obtained PPG signal may be determined to be consistent.

In an embodiment, a consistent portion of a PPG signal may be found by analyzing interpeak distances (e.g., the time-distance between consecutive signal peaks). In an embodiment, an interpeak distance of an obtained PPG signal may be determined and compared to one or more additional interpeak distances. In an embodiment, the first interpeak distance may be compared to a threshold. If it is determined that the first interpeak distance exceeds the threshold, the first interpeak distance may be compared to past and future interpeak distance values. In an embodiment, a portion of the obtained PPG signal corresponding to an inconsistent interpeak distance is removed from the PPG signal. In an embodiment, if it is determined that the first interpeak distance does not exceed a threshold, the corresponding portion of the PPG signal may be determined to be consistent and used to determine one or more parameters inferable from the obtained PPG signal. For example, the respiration rate of a patient may be determined based on a portion of the PPG signal that is determined to be consistent.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
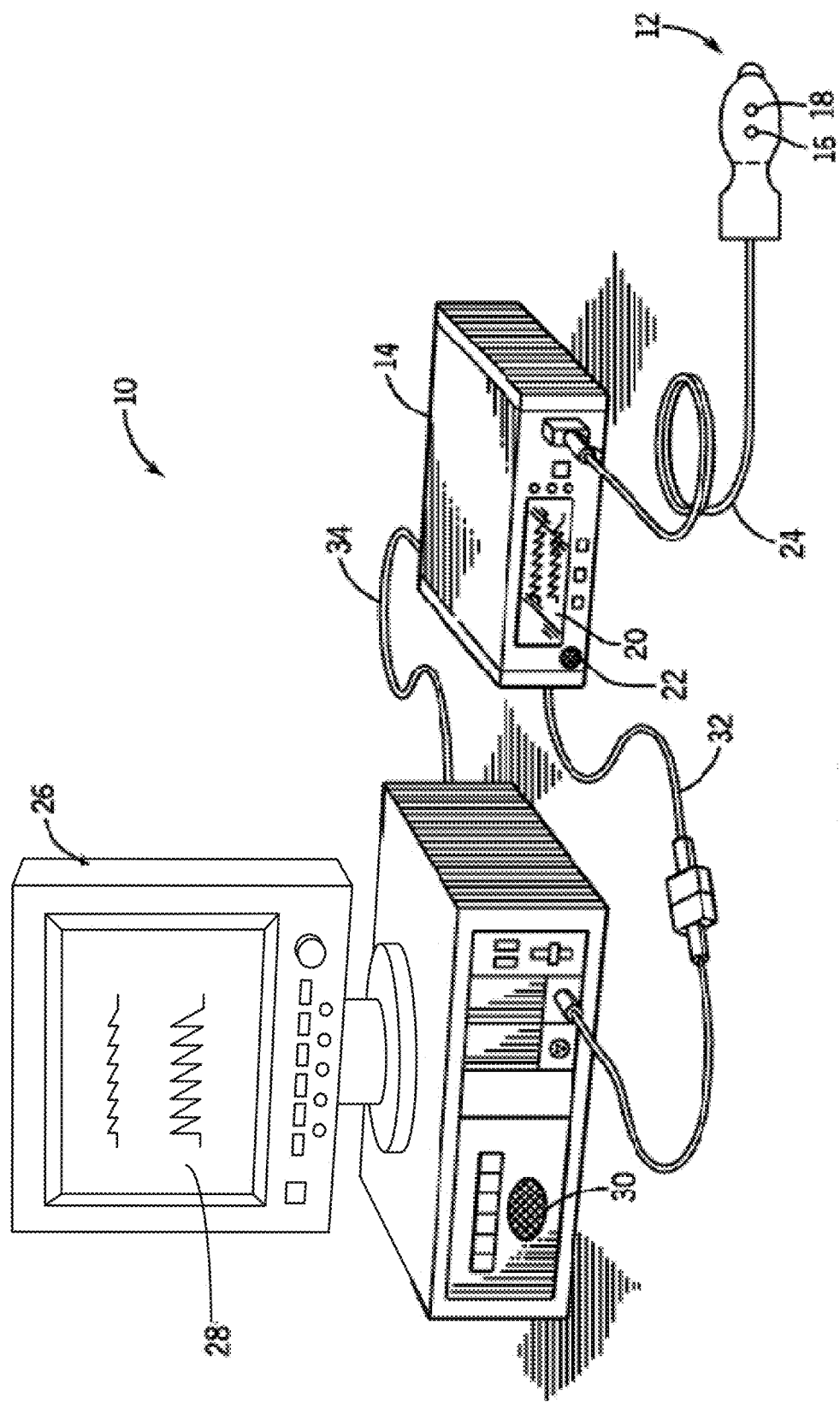
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
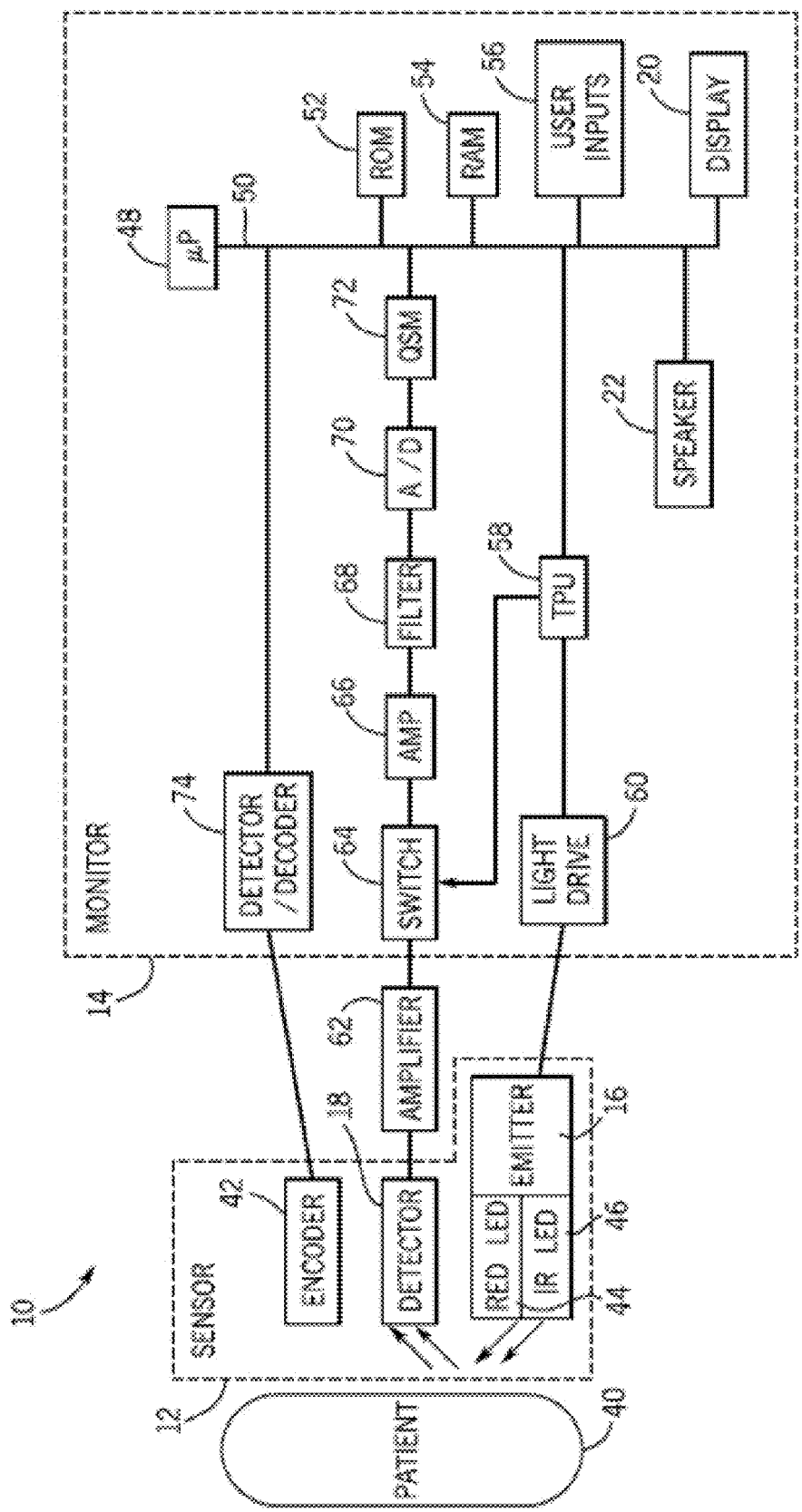
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40.

Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals. PPG signals may be taken herein to mean processed or filtered PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t) \psi^* \left( \frac{t-b}{a} \right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figures 3A, 3B:
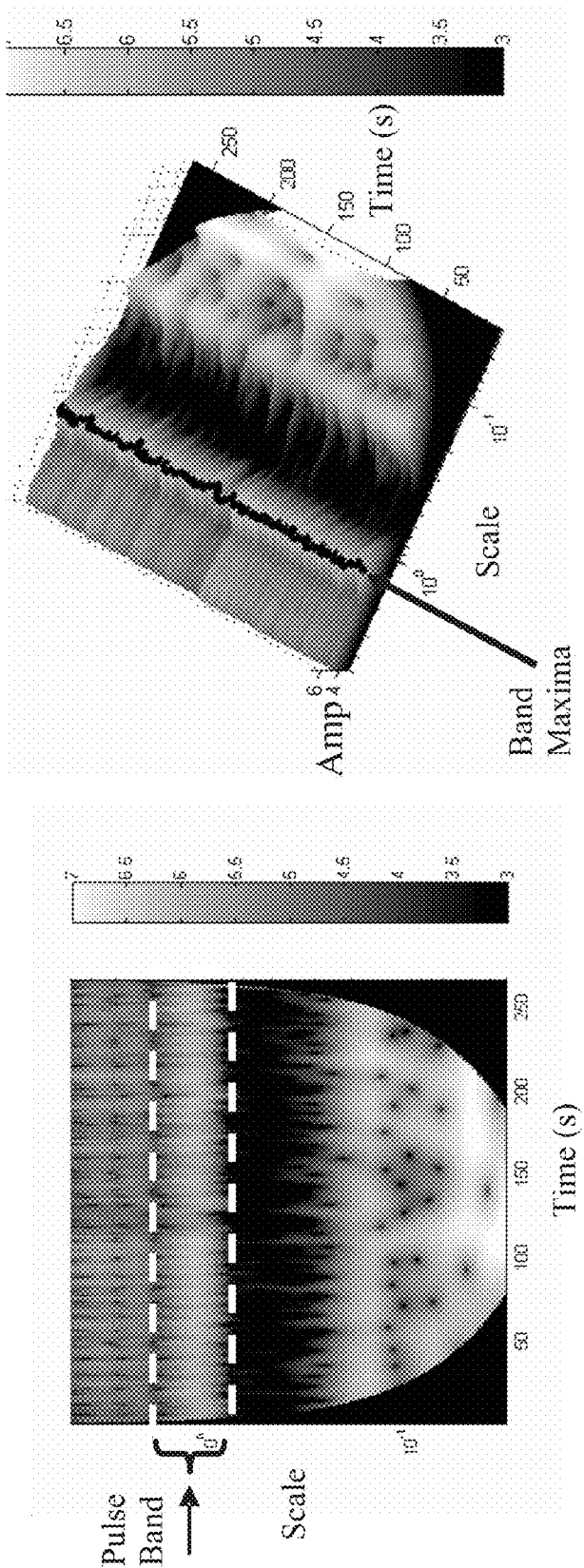
FIGS. 3(a) and 3(b) show illustrative views of a scalogram derived from a PPG signal in accordance with an embodiment.

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
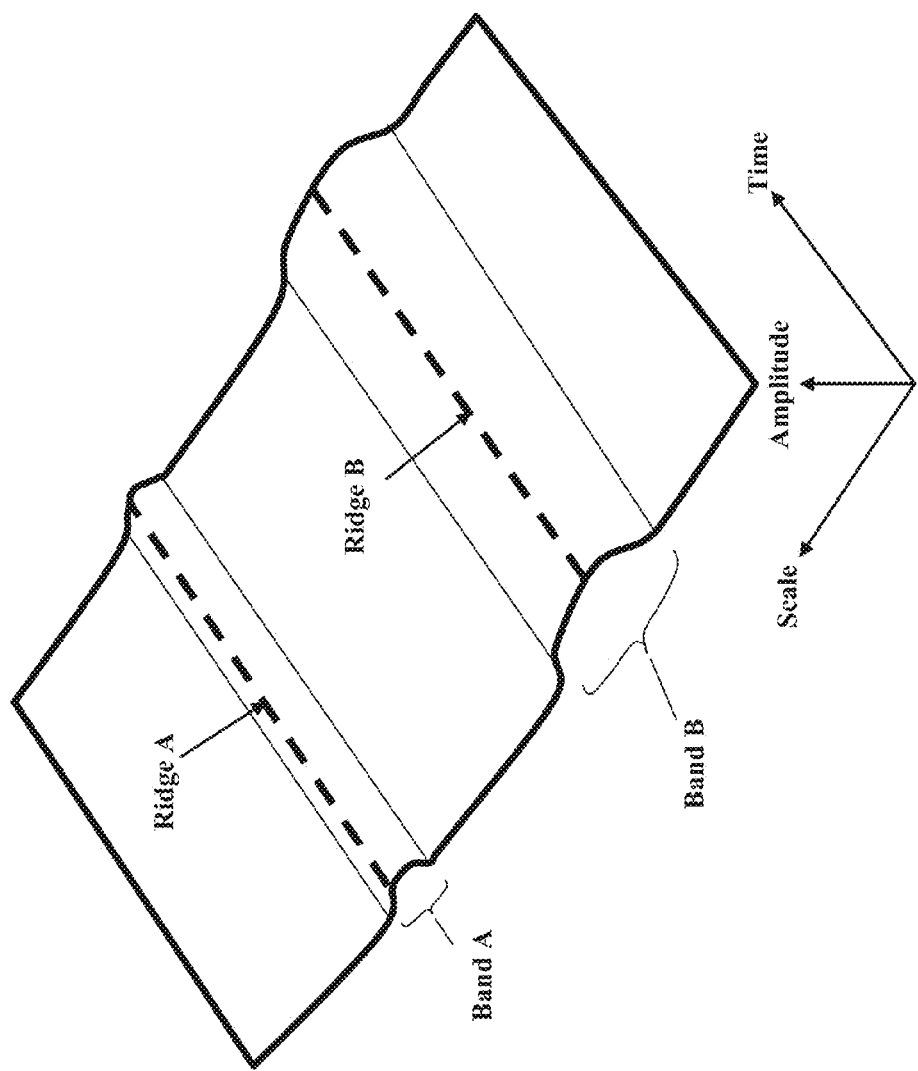
FIG. 3(c) shows an illustrative scalogram derived from a signal containing two pertinent components in accordance with an embodiment.
Figure 3D:
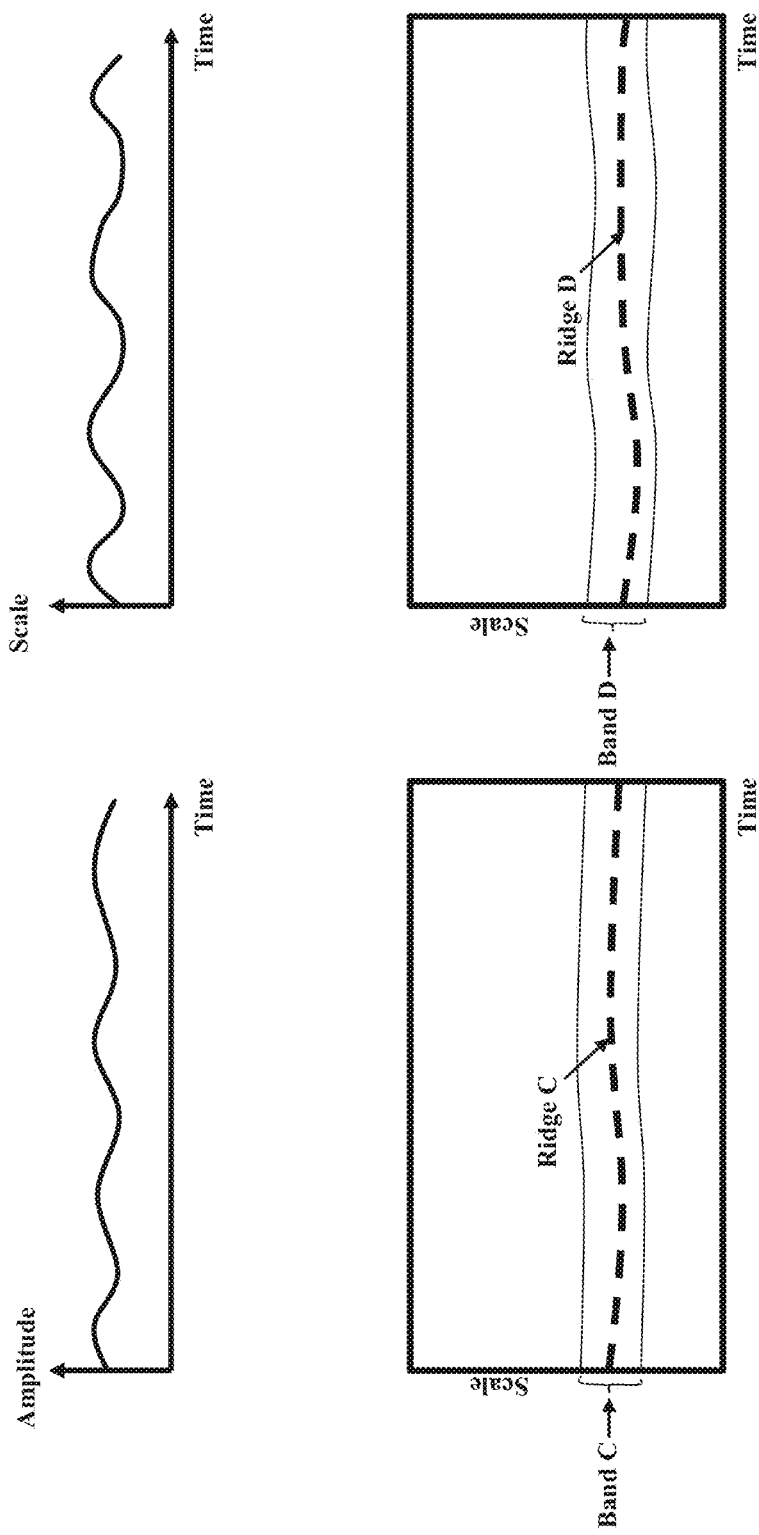
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a, b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
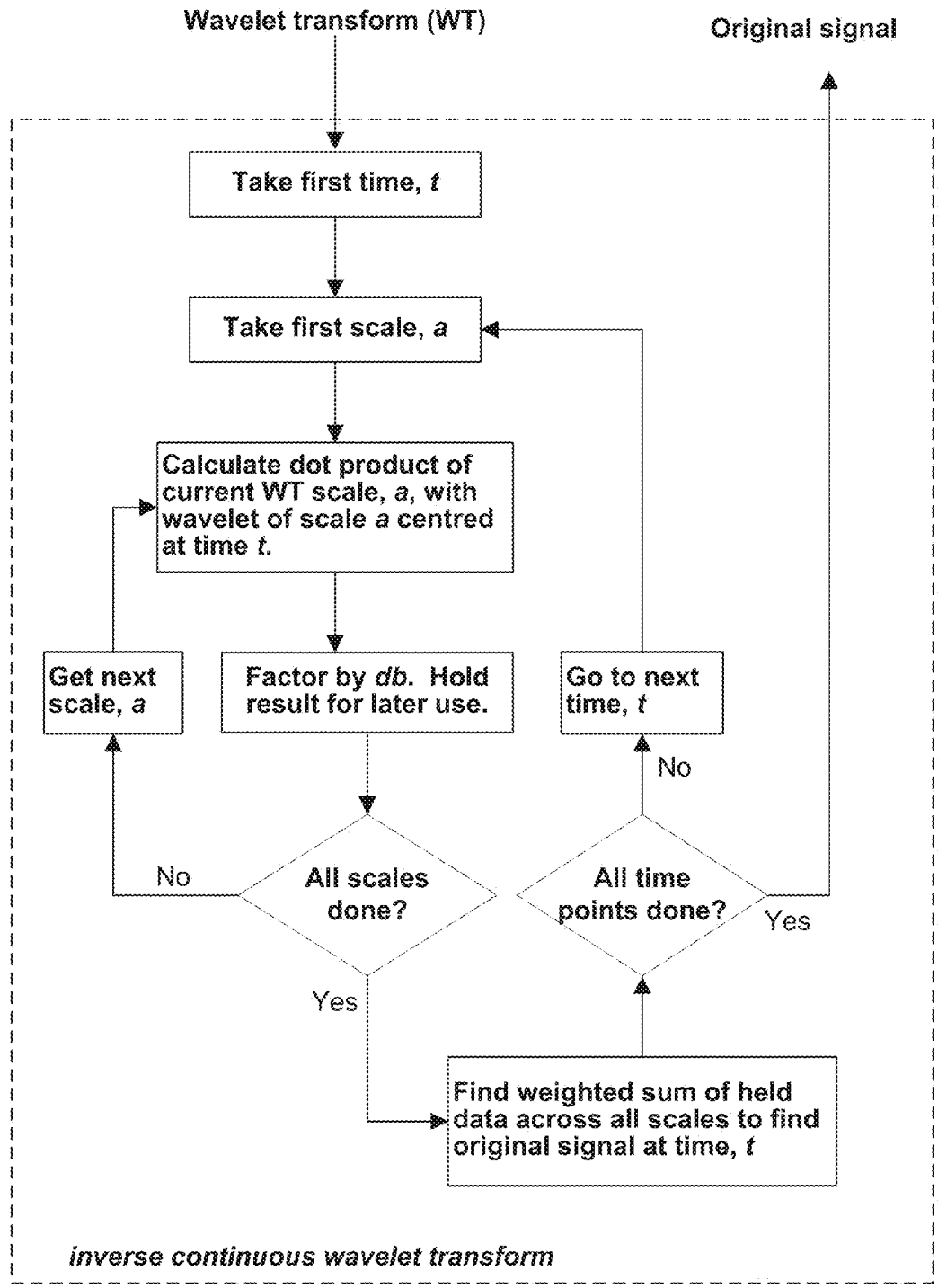
FIGS. 3(e) and 3(f) are flow charts of illustrative steps involved in performing an inverse continuous wavelet transform in accordance with embodiments.
Figure 3F:
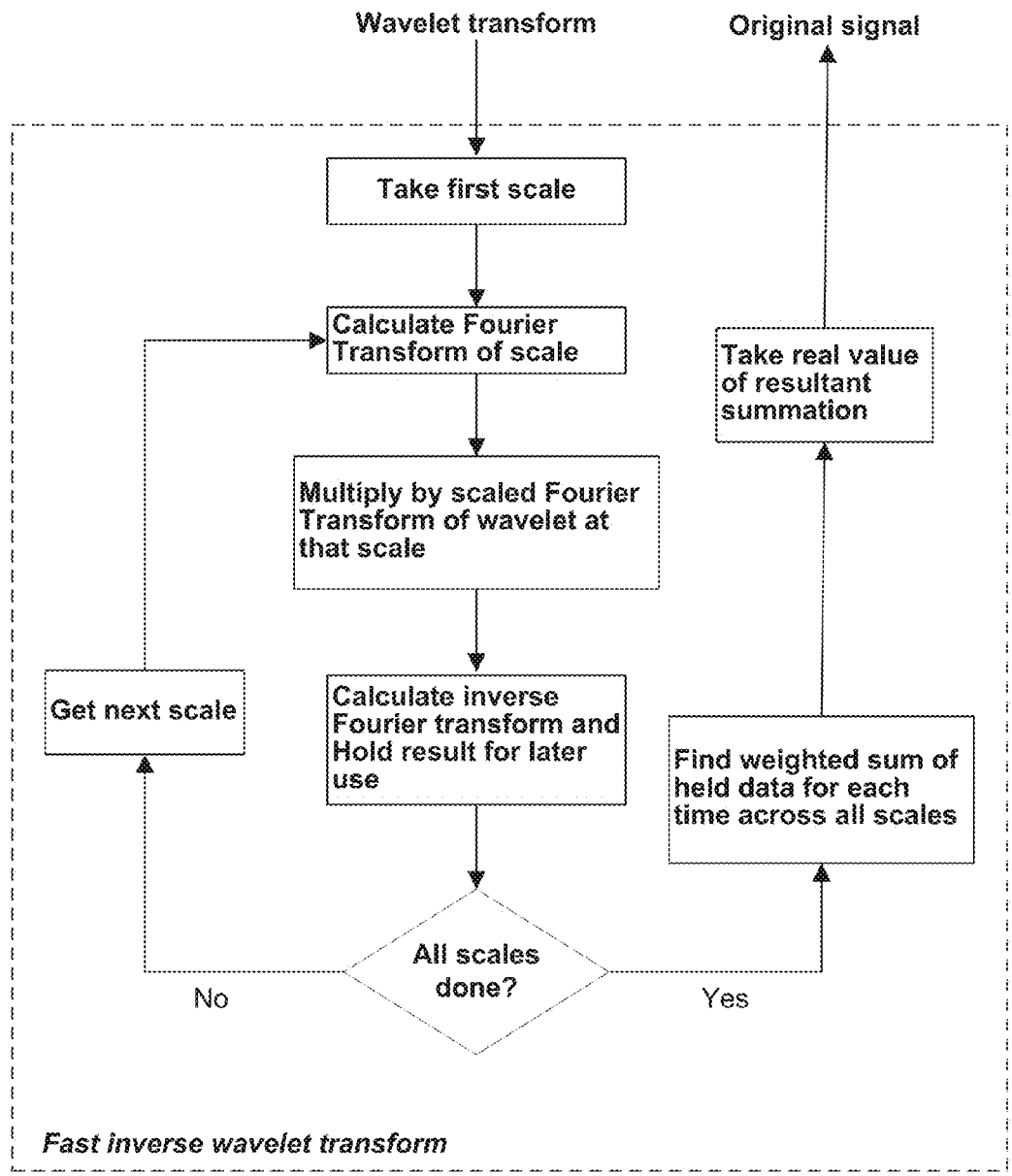

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
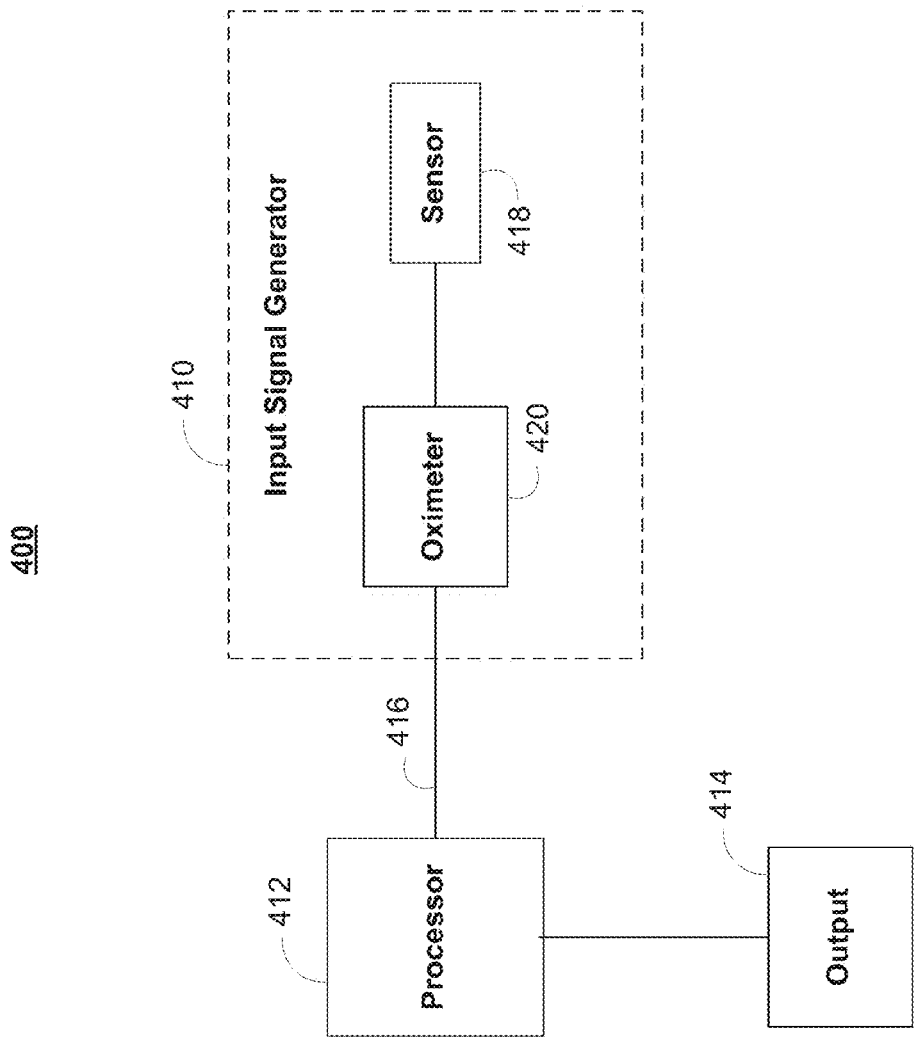
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
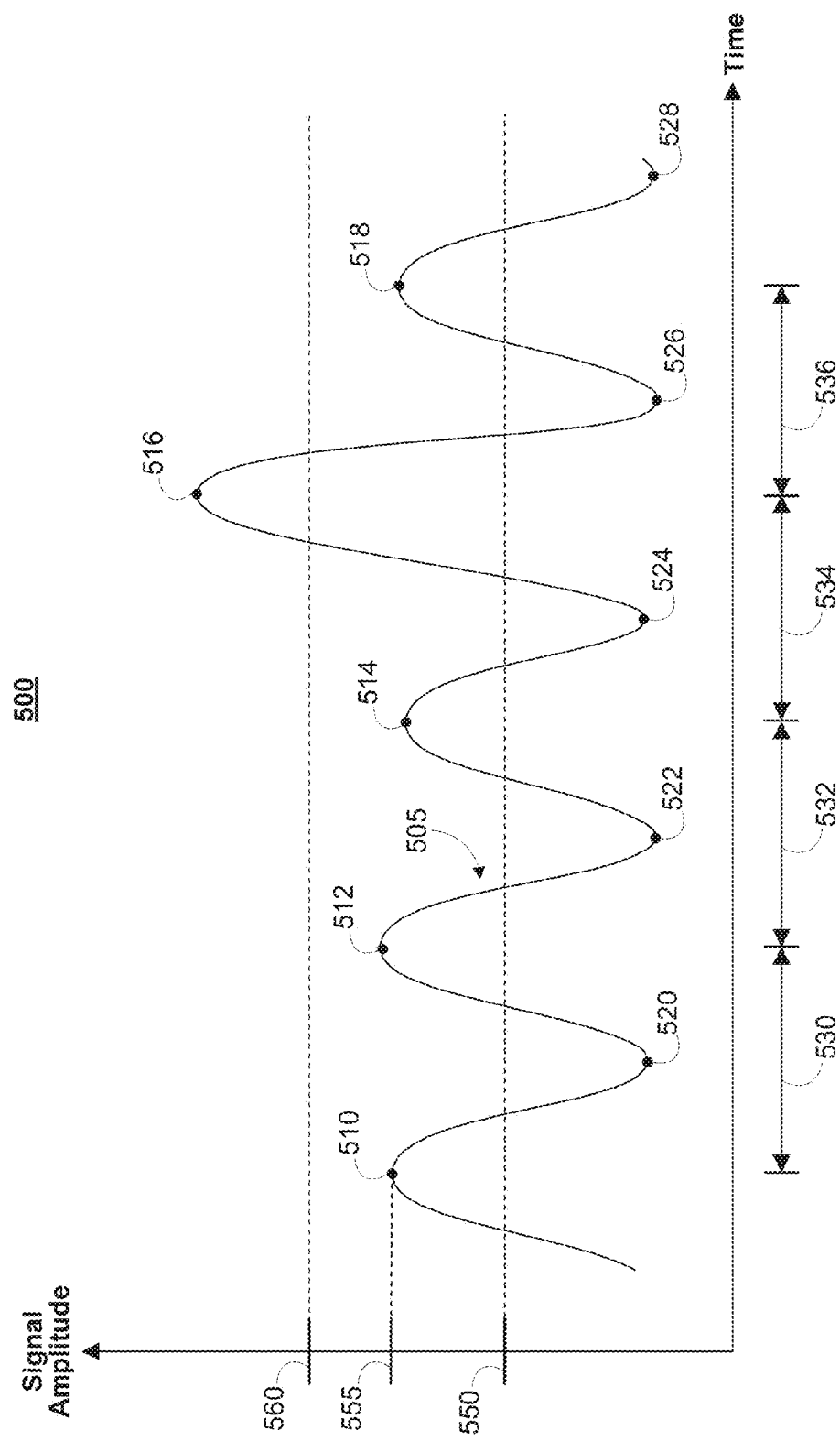
FIG. 5 is an illustrative plot of a PPG signal that may obtained from a pulse oximetry system in accordance with an embodiment.

FIG. 5 is an illustrative plot of a PPG signal that may obtained from pulse oximetry system, including pulse oximetry system 10 (FIG. 1). Plot 500 displays time on the x-axis and signal amplitude values of a PPG signal 505 on the y-axis. PPG signal 505 may be obtained from a patient, such as patient 40 (FIG. 2), using a sensor such as sensor 12 (FIG. 1). Alternatively, PPG signal 505 may be obtained by averaging or otherwise combining multiple signals derived from a suitable sensor array, as discussed in relation to FIG. 1. Plot 500 may be displayed using any suitable display device such as, for example, monitor 20 (FIG. 1), display 28 (FIG. 1), a PDA, a mobile device, or any other suitable display device. Additionally, plot 500 may be displayed on multiple display devices.

PPG signal 505 may exhibit an oscillatory behavior versus time, and may include several undulations of varying signal amplitude level and frequency. The size, shape, and frequency of the undulations of PPG signal 505 may be indicative of an underlying parameter or phenomenon that is to be detected or estimated. For example, PPG signal 505 may reflect the breaths or breathing cycle of a patient, such as patient 40 (FIG. 2), and/or may be used determine the respiration rate of the patient. PPG signal 505 may be a processed version of a preliminary PPG signal obtained by, e.g., sensor 12 (FIG. 1). PPG signal 505 may contain erroneous or otherwise undesirable artifacts due to, for example, patient movement, equipment failure, and/or various noise sources. For example, cable 24, cable 32, and/or cable 34 (all of FIG. 1) may malfunction or become loosened from the equipment to which it is connected. Further, sensor 12 (FIG. 1), or any constituent component of sensor 12 (FIG. 1) (for example, emitter 16 (FIG. 1) and/or detector 18 (FIG. 1)) may malfunction and/or become loosened. Additionally, noise sources may produce inconsistent features in PPG signal 505. Possibly sources of noise include thermal noise, shot noise, flicker noise, burst noise, and/or electrical noise caused by light pollution. These and other noise sources may be introduced, for example, through sensor 12 (FIG. 1), and/or cables 24, 32, and 34 (all of FIG. 1). These and/or other phenomena may be present in a system such as pulse oximetry system 10 (FIG. 1), and thus may introduce inconsistent features into the measured PPG signal 505.

It may be advantageous to select the consistent parts of PPG signal 505 prior to determining (e.g., detecting or estimating) an underlying parameter, such as the respiration rate of a patient, from PPG signal 505. The consistent parts of PPG signal 505 may be used to accurately determine the underlying parameter, at least because the consistent parts of PPG signal 505 may include relative low noise and or be time-invariant with respect to the value of the underlying parameter. Further, the consistent parts of PPG signal 505 may exhibit statistical regularity, and/or may other features that match closely or identically the features used to derive signal processing algorithms, including parameter detection and estimation algorithms. Therefore, such signal processing algorithms may exhibit relatively strong performance, e.g., detection or estimation performance, when applied to the consistent parts of PPG signal 505. To select consistent parts of PPG signal 505, several features of the signal may be used. For example, signal peaks 510, 512, 514, 516, and 518 may be identified and used to determine consistency. Alternatively or additionally, signal troughs 520, 522, 524, 526, and/or 528 may be used. In an embodiment, the interpeak distances 530, 532, 534, and 536 may be used. In an embodiment, the peaks of the first, second, or any other suitable derivative of PPG signal 505 may be used to determine consistency. These and other features and characteristic points of PPG signal 505 may be used separately or in combination to select a consistent part (or parts) of PPG signal 505. For example, process 600 (depicted in FIG. 6) illustrates exemplary techniques for selecting a consistent portion of PPG signal 505 for further analysis using properties of signal peaks, e.g., signal peaks 510, 512, 514, 516, and/or 518. Processes 700 and 725 (of FIG. 7A and FIG. 7B, respectively) may show further embodiments of process 600 (FIG. 6) in which the peak amplitude levels of PPG signal 505, e.g., signal peaks 510, 512, 514, 516, and/or 518, are used to select a consistent part (or parts) of PPG signal 505. Process 800 (of FIG. 8) may show a further embodiment of process 600 (FIG. 6) for which the time-distance between signal peaks, e.g., interpeak distances 530, 532, 534, and/or 536 are used to select a consistent part (or parts) of PPG signal 505 for further analysis.

Although the techniques disclosed herein are described in terms of PPG signal 505, the disclosed techniques may be applied to any other suitable signal. For example, the disclosed techniques may be applied to other biological signals (i.e., biosignals) including transthoracic impedance signals, and/or capnograph signals. Further, PPG signal 505 or any other related signal may be obtained from a source other than pulse oximeter system 10 (FIG. 1) For example, PPG signal 505 may be obtained from another type of medical device or from non-medical devices including a general signal oscilloscope and/or waveform analyzer. PPG signal 505 may be a simplified embodiment of a PPG signal, or other type of signal, measured in practice. The techniques disclosed herein may be applied to signals that, e.g., have more or less frequent undulations than PPG signal 505, time-variant mean amplitude values, noise patterns, and/or discontinuities. The techniques described herein may be applied to PPG signals that do not resemble the time-varying pattern of PPG signal 505 shown in FIG. 5.

Figure 6:
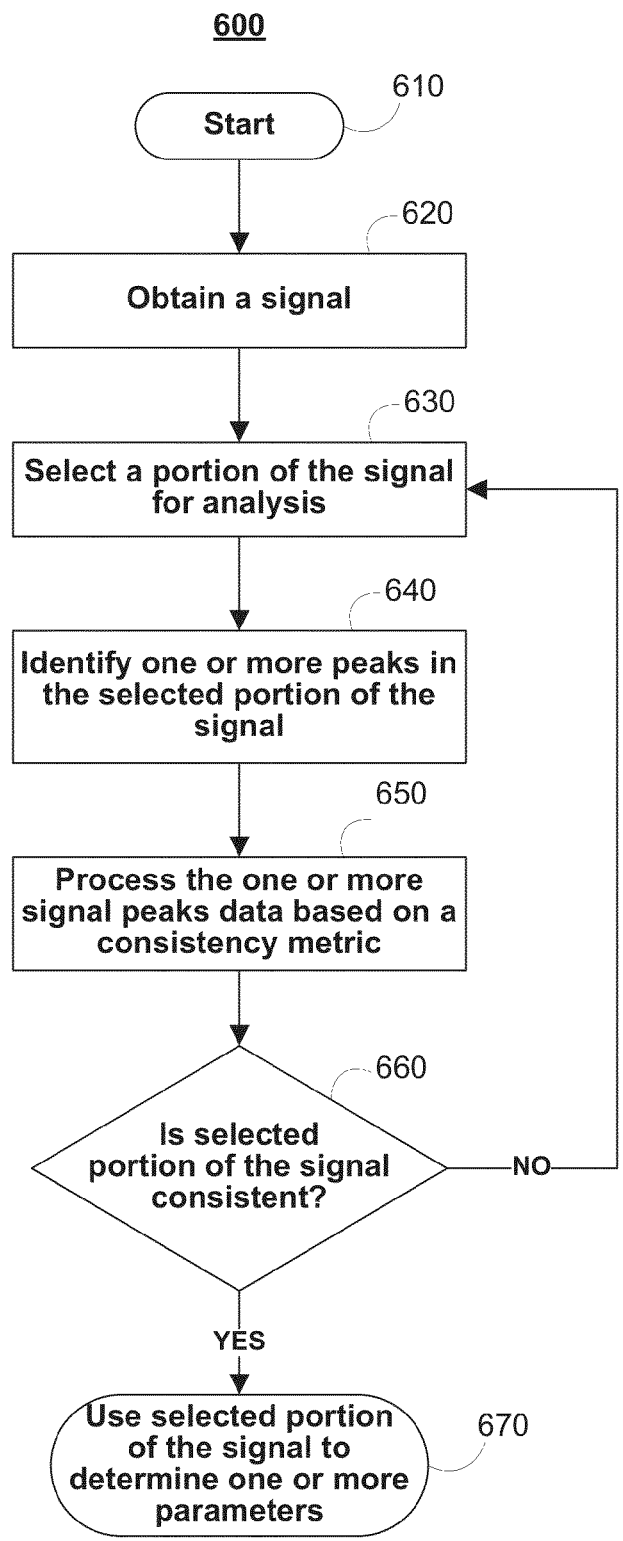
FIG. 6 depicts an illustrative process for selecting a consistent part (or parts) of a signal, such as a PPG signal, by analyzing properties of signal peaks.

FIG. 6 depicts an illustrative process for selecting a consistent part (or parts) of a signal, e.g., PPG signal 505 (FIG. 5), by analyzing properties of signal peaks (i.e., peaks in the signal amplitude values) in accordance with an embodiment. Process 600 may be used to select and analyze a portion of the obtained signal for further analysis, including the determination (e.g., detection or estimation) of underlying signal parameters, such as the respiration rate of a patient (e.g., patient 40 (FIG. 2)). For example, process 600 may be used to determine a most consistent portion of a signal, in terms of a consistency metric. Process 600 may be implemented in a pulse oximetry system such as pulse oximetry system 10 (FIG. 1), and the steps of process 600 may be carried out using a processor such as processor 412 (FIG. 4) or microprocessor 48 (FIG. 2).

Process 600 may start at step 610. At step 620, process 600 may obtain a signal. The obtained signal may be a PPG signal such as PPG signal 505 (FIG. 5) or any other suitable biosignal or general signal. The signal may be obtained from pulse oximetry system 10 (FIG. 1) using a sensor such as sensor 12 (FIG. 1) to measure biological characteristics of a patient such as patient 40 (FIG. 2). Additionally, the obtained signal may be a real-time signal or it may be a signal previously obtained and stored in memory, for example, ROM 52 (FIG. 2) or RAM 54 (FIG. 2).

The signal obtained at step 620 may be obtained by first obtaining a preliminary PPG signal and processing the preliminary PPG signal. The preliminary PPG signals may be obtained using, e.g., sensor 12 (FIG. 1) and processed using a processor such as processor 412 (FIG. 4) or microprocessor 48 (FIG. 2) to compute, e.g., the respiration rate of patient 40 (FIG. 2) in a system similar or identical to pulse oximetry system 10 (FIG. 1). For example, to obtain a signal at step 620, process 600 may detect and process the up and down strokes of a preliminary PPG signal using techniques similar or identical to those described in Watson, U.S. Provisional Application No. 61/077,092, filed Jun. 30, 2008, entitled "Systems and Method for Detecting Pulses," which is incorporated by reference herein in its entirety. In an embodiment, one or more preliminary PPG signals may be selected and mirrored to create the signal obtained at step 620. The preliminary PPG signals may contain one or more repetitive components. In an embodiment, a portion of a preliminary PPG signal is selected and mirrored to reduce undesirable artifacts caused by the non-selected portion of the preliminary PPG signal. In an embodiment, additional portions of the preliminary PPG signal may be selected, mirrored, and added to create the signal obtained at step 620. In an embodiment, Secondary Wavelet Feature Decoupling (SWFD) may be used on one or more preliminary PPG signals to create the signal obtained at step 620. In an embodiment, regions of preliminary PPG signals may be selected and concatenated using techniques similar or identical to those described in McGonigle et al., U.S. Patent Publication No. 2009/0326831, published Dec. 31, 2009, which is incorporated by reference herein in its entirety.

At step 630, a portion of the signal obtained in step 620 may be selected for analysis. For example, a time-window may be applied to the signal obtained in step 620 by a processor such as processor 412 (FIG. 2) or microprocessor 48 (FIG. 2) to select a portion of the signal. At step 640, one or more signal peak values may be identified from the portion of the signal selected at step 630. For example, the first two or first three signal peak values may be selected. Signal peak values may be found, e.g., using any suitable signal processing technique, including a zero-crossing technique, a root-finding technique, an analytic curve-fitting technique, and/or a numerical analysis of the derivatives of the selected portion of the signal. These and other techniques may be implemented in pulse oximetry system 10 (FIG. 1) by processor 412 (FIG. 2), microprocessor 48 (FIG. 2), ROM 52 (FIG. 2), and/or RAM 54 (FIG. 2). Additionally, the parameters that may be used by suitable signal processing techniques, e.g., tolerance values and sensitivity levels, may be controlled by a user or patient using, e.g., using user inputs 56 (FIG. 2). Signal peaks that are identified may be displayed, for example, on monitor 26 (FIG. 1) or display 20 or 28 (both of FIG. 1). Alternatively, the portion of the signal selected at step 630 may be displayed on a monitor, and a user may choose or otherwise influence which peaks are selected using, for example, user inputs 56 (FIG. 2).

At step 650, peaks identified in current and past iterations of step 640 of process 600 may be processed according to a consistency metric. For example, the consistency metric may specify a target number of suitable signal amplitude peaks (e.g., three peaks). In this case, signal peak values may be processed until three consecutive signal peaks have been identified, as further described according to particular embodiments by process 700 (FIG. 7A) and process 725 (FIG. 7B). Alternatively or additionally, the consistency metric may specify a target number of suitable interpeak distances using a process or processes similar or identical to process 800 (FIG. 8). Further, a metric or metrics may be computed using the identified peak values to characterize the suitability of the selected portion of the signal determined at step 630. Exemplary metrics may include the median signal peak amplitude value, mean signal peak amplitude value, standard deviation of the signal peak amplitude values, and/or the average signal interpeak distance.

At step 660, the processed peak data obtained at step 640 may be compared to the consistency metric to determine if signal obtained at step 620 is consistent. For example, if the consistency metric specifies three signal peaks having amplitude levels within a certain range, then the processed peak data determined at step 650 may be compared to this condition (i.e., consistency metric) at step 660. At step 670, the selected portion of the signal determined in step 630, or a processed version, may be used for further analysis. For example, the signal may be used to determine a rate of occurrence of certain features, such as a respiration rate of a patient (e.g., patient 40 (FIG. 2)). For example, one embodiment of step 630 is illustrated by process 900 (FIG. 9), where a patient respiration rate may be determined. If at step 660, a portion of the signal selected at step 630 is determined not to be consistent, process 600 may return to step 630. At step 630, process 600 may obtain a new portion of the signal previous obtained at step 620. Alternatively, and not shown in FIG. 6, process 600 may return to step 620, and obtain a new signal for analysis.

Figure 7A:
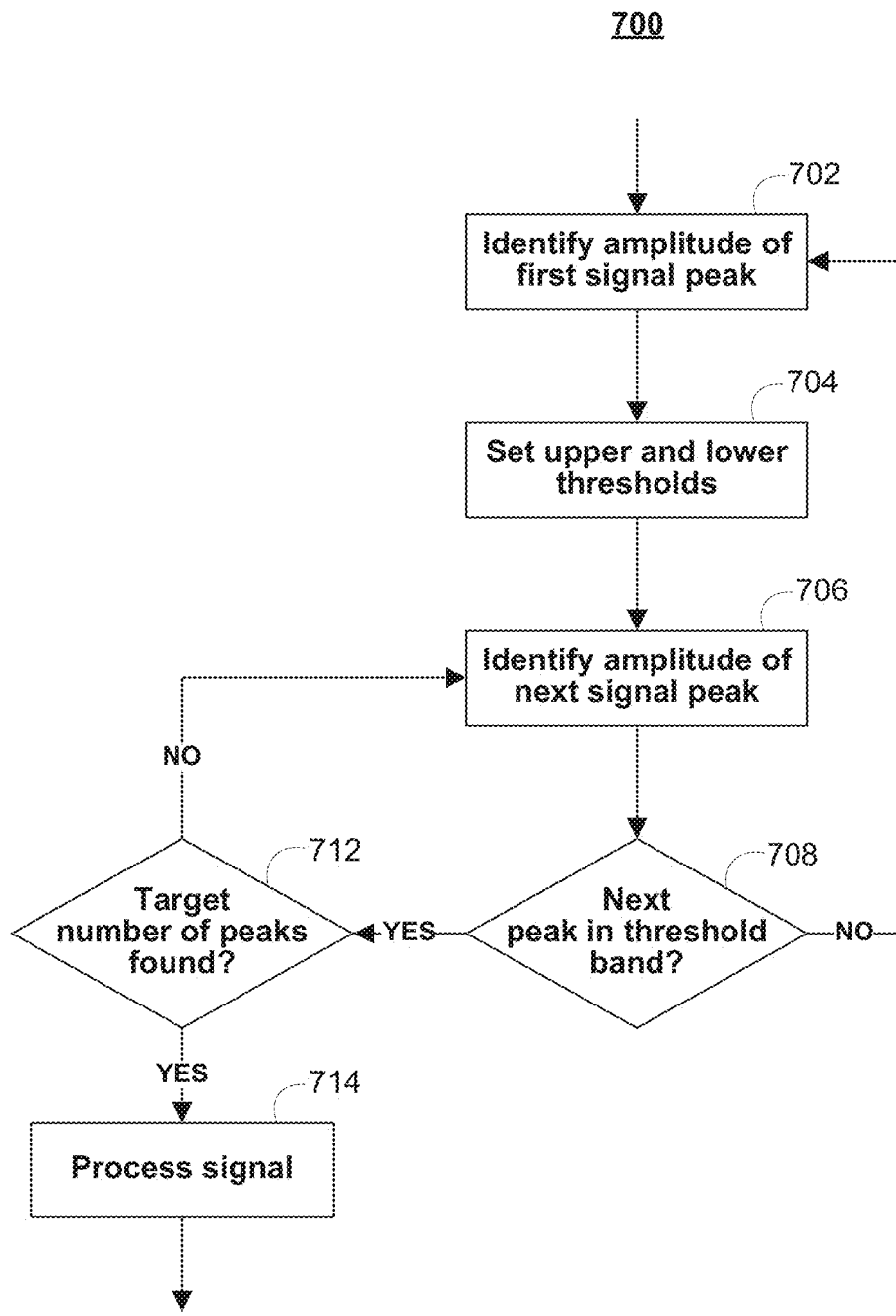
FIGS. 7A-7C depict illustrative processes for selecting a consistent part (or parts) of a signal, for example, a PPG signal, by analyzing the amplitudes of signal peaks in accordance with some embodiments.
Figure 7B:
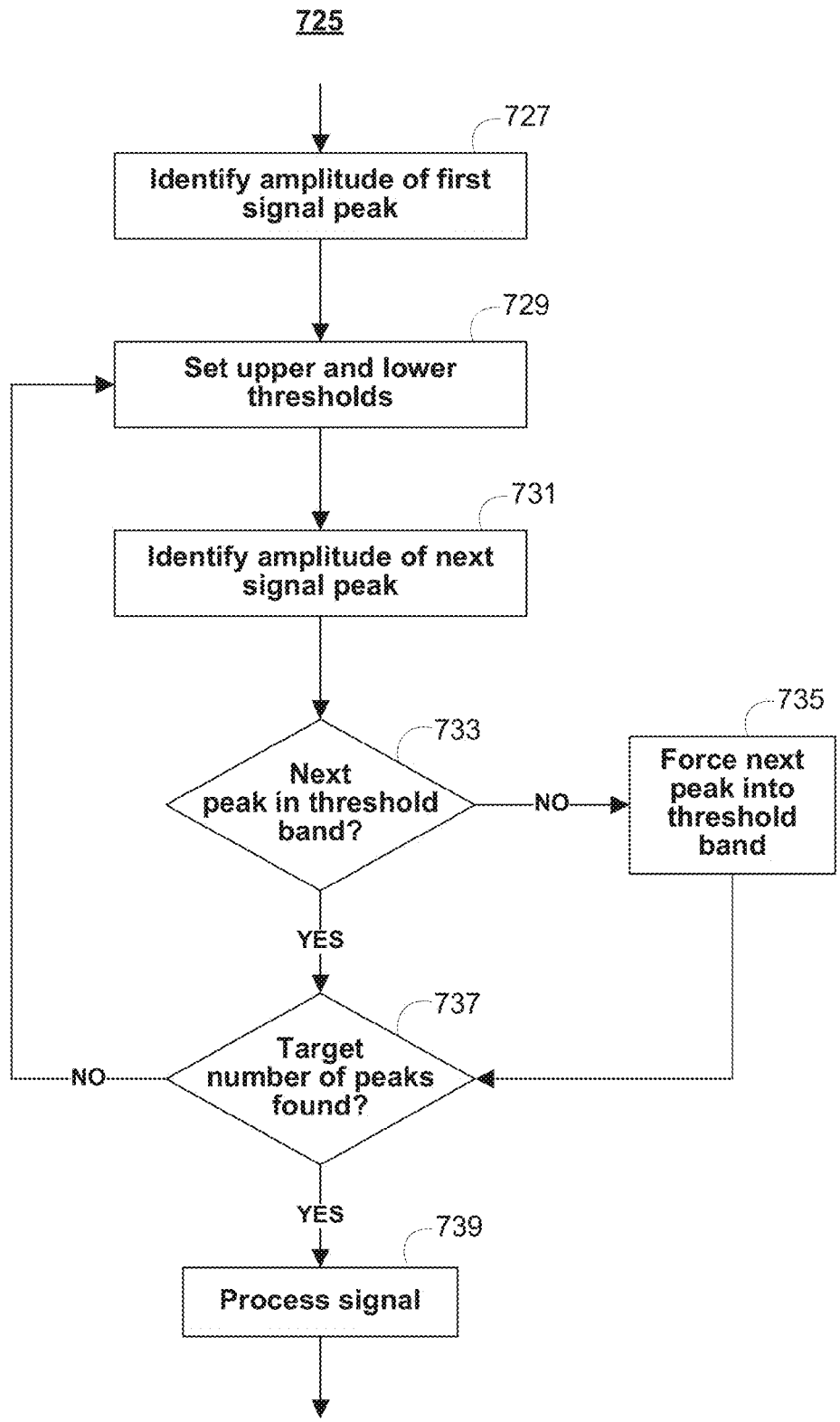
Figure 8:
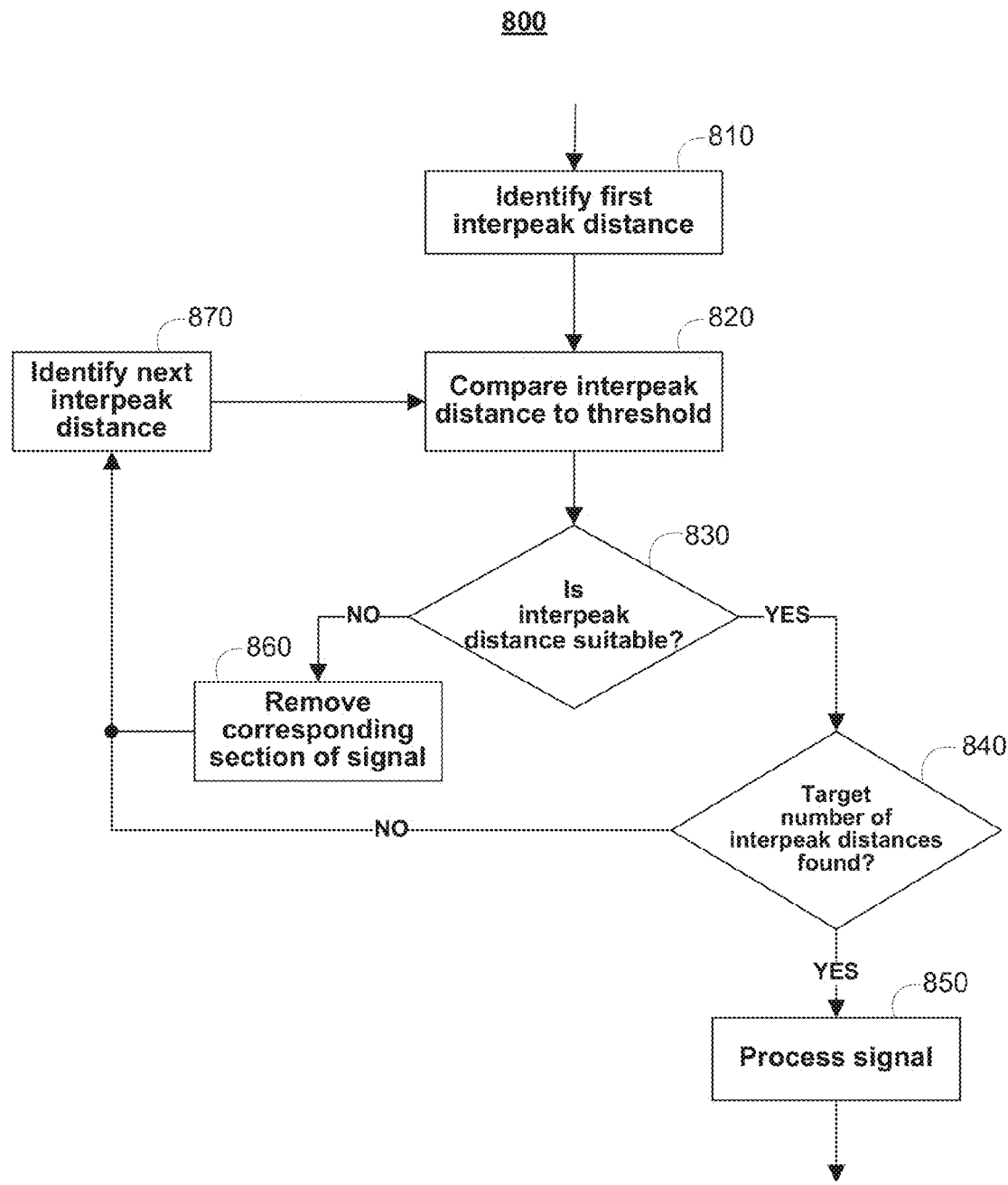
FIG. 8 depicts an illustrative process for selecting a consistent part (or parts) of a signal, for example, a PPG signal, by analyzing the periods between signal peaks.

FIG. 7A depicts an illustrative process for selecting a consistent part of a signal, e.g., PPG signal 505 (FIG. 5), by analyzing the amplitudes of signal peaks in accordance with some embodiments. Process 700 may correspond to a further embodiment of process 600, and more particularly, may correspond to a further embodiment of step 650 of FIG. 6. Process 700 may operate according to amplitude-based consistency metric that specifies upper and lower thresholds, and that determines a target number of consecutive signal peaks, all having amplitude values within the amplitude range specified by the upper and lower thresholds. Process 700 may be referred to as a consistency in amplitude technique.

Process 700 may start at step 702. At step 702, the amplitude of a first signal peak may be identified. For example, at step 702, process 700 may search a signal obtained by process 600 (FIG. 6) at step 620 (FIG. 6), and/or that may have been generated by a signal generator such as signal generator 410 (FIG. 4). The location of the first signal peak may be determined using a method similar or identical to the signal processing methods described in relation to step 640 (FIG. 6). The first signal peak may correspond to the first-occurring signal peak in time, e.g. signal peak 510 (FIG. 5) of PPG signal 505, and/or it may correspond to the first signal peak found through a suitable signal processing algorithm, such as an extrema-finding algorithm. Once the location of a first peak has been found, step 702 may identify the amplitude of the first signal peak, for example, using microprocessor 48 (FIG. 2) or processor 412 (FIG. 4).

At step 704, upper and lower thresholds may be set relative to the amplitude of the signal peak identified in step 702. In an embodiment, an upper threshold may be set at an amplitude value larger than the amplitude of the first signal peak, and a lower threshold may be set at an amplitude value lower than the amplitude of the first signal peak. For example, for PPG signal 505 (FIG. 5), the first signal peak may be identified as signal peak 510 (FIG. 5), which has corresponding signal peak amplitude value 535 (FIG. 5). In this case, the lower threshold may be set at amplitude value 550 (FIG. 5), and an upper threshold may be set at amplitude value 560 (FIG. 5). The range of amplitude values between the lower threshold amplitude value 550 (FIG. 5) and the upper threshold amplitude value 560 (FIG. 5) may be referred to as the threshold region or threshold band. For example, in FIG. 5, the threshold region (or threshold band) may consist of all the amplitude values between amplitude value 550 (FIG. 5) and amplitude value 560 (FIG. 5). Process 700 may then continue to step 706. At step 706, the amplitude of a next signal peak may be identified. For example, for PPG signal 505, the amplitude of the signal peak 512 (FIG. 5) may be identified (signal peak 512 being the neighbor of signal peak 510 (FIG. 5)). Alternatively, the amplitude of any of the signal peaks 514, 516, or 518 (all of FIG. 5) may be identified as the next signal peak. The particular signal peak identified as the next signal peak at step 706 may depend on, e.g., a numerical search algorithm performed by a processor such as processor 412 (FIG. 4) or microprocessor 48 (FIG. 1).

At step 708, process 700 may determine if the amplitude of the signal peak identified in step 706 lies within a threshold region. For example, signal peak 512 (FIG. 5) may be identified at step 706, and at step 708, process 700 may determine if the amplitude of signal peak 512 (FIG. 5) lies within the threshold region defined by amplitude values 550 and 560 (FIG. 5). If the amplitude of the signal peak identified in step 706 lies within the threshold region, process 700 may continue to step 712. Otherwise, process 700 may return to step 702.

At step 712, process 700 may determine if a target number (or predetermined number) of consecutive signal peaks have been found through consecutive iterations of process 700, for which the amplitudes of the consecutive signal peaks all lie within the threshold region. For example, process 700 may operate on PPG signal 505 (FIG. 5), and may specify a target number of three (or any other suitable number) of signal peaks. Process 700 may then determine if three consecutively identified signal peaks have been found, for which the amplitude of each signal peak lies within the threshold region. For example, step 712 may analyze signal peaks 510, 512, and 514 (of FIG. 5), which may have been determined at step 702, a first iteration of step 706, and a second iteration of step 706, respectively, to determine if each signal peak lies within the threshold region specified by amplitude values 550 and 560. If the target number of signal peaks has not been found (e.g., if only signal peak values 510 and 512 have been found in FIG. 5 and if the target number of signal peaks is three), process 700 may return to step 706 where a next signal peak is considered to see if it too lies within the threshold region (e.g., signal peak 514). Therefore, process 700 may continue to search for signal peaks until the amplitude of a signal peak lies outside the threshold region (in which case, process 700 may return to step 702), or until a target number of signal peaks have been found. If, at step 712, the target number of signal peaks has been found, process 700 may continue to step 714. At step 714, process 700 may normalize the portion of the signal corresponding to the signal peaks (i.e., the consistent part of the signal). For example, process 700 may filter the signal corresponding to the signal peaks to normalize signal peak values, remove noise-artifacts, and/or perform curve smoothing and interpolation operations.

If, at step 708, the amplitude of signal peak is determined not to lie within the threshold region (for example, in FIG. 5, signal peak 516 does not lie within the threshold region defined by amplitude values 550 and 560), process 700 may return to step 702. At step 702 a new first peak for analysis may be identified. For example, a new first peak may be identified by considering a different portion of the same signal considered in a previous iteration of step 702, and/or by obtaining and analyzing a new signal. For example, in FIG. 5, signal peak 516 may be analyzed at step 708, and process 700 may return to step 702 as signal peak 516 lies outside the threshold region defined by amplitude levels 550 and 560. At step 702, signal peak 518, may be selected as the first signal peak in a subsequent iteration of process 700.

Process 700 may be used to identify the most signal peaks using the lowest threshold values and/or the smallest threshold region. Consecutive iterations of process 700 may fail to produce the target number of desired signal peaks, or it may produce signal peaks infrequently. Process 700 may increase the number and/or frequency of identified signal peaks by, for example, increasing the breadth of the threshold region by raising the upper threshold amplitude value and lowering the lower threshold amplitude value simultaneously. This may increase the number of signal peaks counted in the threshold region (e.g., the threshold region defined by amplitude values 550 and 560 in FIG. 5). This process may also be repeated for each signal peak and for larger threshold regions.

In an alternative embodiment, process 700 may, as a first step, identify all of the signal peaks within a given threshold region. For example, process 700 may be used to analyze PPG signal 505 (FIG. 5). In this case, process 700 may initially identify all of the signal peaks that lie within the threshold region defined by amplitude values 550 and 560 (FIG. 5). Process 700 may then count the total number of signal peaks (e.g., the total number of consecutive signal peaks) occurring within this threshold region. For example, process 700 may identify a total of four signal peaks within the threshold region defined by amplitude values 550 and 560 (FIG. 5). In general, process 700 may count a number of signal peaks equal to or greater than the target number of signal peaks, or process 700 may count a number of signal peaks less than the target number of signal peaks. In the latter case, the width of the threshold region may be increased, and the process 700 may recount the number of signal peaks located within this expanded threshold region. For example, if the target number of signal peaks corresponding to PPG signal 505 (FIG. 5) using the threshold region defined by amplitude values 550 and 560 (both of FIG. 5) is five or more, then process 700 will find fewer than the target number of signal peaks. In this case, the threshold region of FIG. 5 may be expanded, and process 700 may recount the number of signal peaks present in the enlarged threshold region. In FIG. 5, the threshold region may be expanded by, for example, increasing the amplitude value of the upper threshold (i.e., to a value larger than amplitude value 560 (FIG. 5)) and/or by decreasing the amplitude value of the lower threshold (i.e., to a value smaller than amplitude value 550 (FIG. 5)).

FIG. 7B depicts another illustrative process for selecting a consistent part of a signal, e.g., PPG signal 505 (FIG. 5), by analyzing the amplitudes of signal peaks in accordance with some embodiments. In contrast to process 700, process 725 may force signal peaks, or other features, that are located outside of the threshold region (e.g., the threshold region depicted in FIG. 5) into a suitable range for further analysis. Process 725 may be advantageous at least for preventing such features from dominating a statistical analysis of a signal trace (e.g., the signal trace of PPG signal 505 versus time shown in FIG. 5). Process 725, may be used to force consistency in an observed signal, for example, PPG signal 505 (FIG. 5), when features lie outside of the threshold region (e.g., signal peak 516 (FIG. 5). Process 725 may correspond to an embodiment of process 600, and may correspond to another embodiment of step 650 of FIG. 6. Process 725 may operate according to amplitude-based consistency metric that specifies upper and lower thresholds, and that determines and/or transforms a target number of consecutive signal peaks, so that all the peaks have amplitude values within the amplitude range specified by the upper and lower thresholds. Process 725 may be referred to a consistency in amplitude technique.

Process 725 may begin at step 727, where the amplitude of a first signal peak (of an obtained signal) may be identified. For example, the amplitude of a first signal peak may be determined similarly or identically to that of step 702 (FIG. 7A). At step 729, upper and lower thresholds may be set relative to the amplitude of the signal peak identified at step 725. For example, lower and upper thresholds may be set similarly or identically to step 704 of process 700 (FIG. 7A). At step 731, the amplitude of a next signal peak may be identified. For example, the amplitude of a next signal peak may be identified using techniques similar or identical to that of step 706 of process 700 (FIG. 7A). Process 725 may then continue to step 733. At step 733, process 725 may determine if the amplitude of the signal peak identified in step 731 lies within the threshold region. For example, process 725 may make this determination using techniques similar or identical to those in step 708 of process 700 (FIG. 7A). If the signal peak amplitude level is determined to lie within the threshold region, process 725 may continue directly to step 737. Otherwise, process 700 may continue to step 735, and then to step 737.

At step 735, process 725 may force the signal peak identified in step 731 to lie within the threshold band. For example, process 735 may uniformly scale the signal peak (and related adjacent signal components) so that the resultant portion of the signal including the modified signal peak lies within the threshold band. Alternatively, process 735 may use quantization, rounding, or any suitable template-matching technique so that the resulting portion of the signal including the signal peak lies within the threshold band. Further, process 725 may, at step 735, remove, splice, transform, or otherwise modify the portion of the signal that lies outside the threshold region, and/or may concatenate the remaining portion of the signal so that the resultant signal is continuous in time.

At step 737, process 725 may determine if a target number (or predetermined number) of consecutive signal peaks have been found. For example, process 725 may operate on PPG signal 510 (FIG. 5), and may have a target of five signal peaks (or any other number of suitable signal peaks). Process 725 may continue until five signal peaks are found, e.g., until signal peaks 510, 512, 514, 516, after processing in step 735, and 518 have been found (signal peaks 510, 512, 514, and 516 are all shown in FIG. 5). If, at step 737, the target number of signal peaks has been found, process 725 may continue to step 739. At step 739, process 725 may further process the portion of the signal corresponding to the signal peaks (i.e., the consistent part of the signal). For example, process 725 may filter the signal corresponding to the signal peaks to further normalize signal peak values, remove noise-artifacts, and/or may perform curve smoothing and interpolation operations of the consistent part of the signal.

If, at step 737, the target number of signal peaks has not been found, process 725 may continue to selected another signal peak by returning to step 729. At step 729, process 725 may reset the upper and lower threshold values. Therefore, upper and lower threshold values may vary over time, e.g., to account for drift in the feature amplitude, period, or general morphology of the obtained signal. Process 725 may then return to step 731, where the amplitude of a next signal peak is identified.

Processes 700 (FIG. 7A) and 725 may also be used in combination or with other modifications to determine a consistent part of an obtained signal. For example, elements of process 725, including, for example, step 735, may be incorporated into process 700 to determine a consistent part of the signal.

Figure 7C:
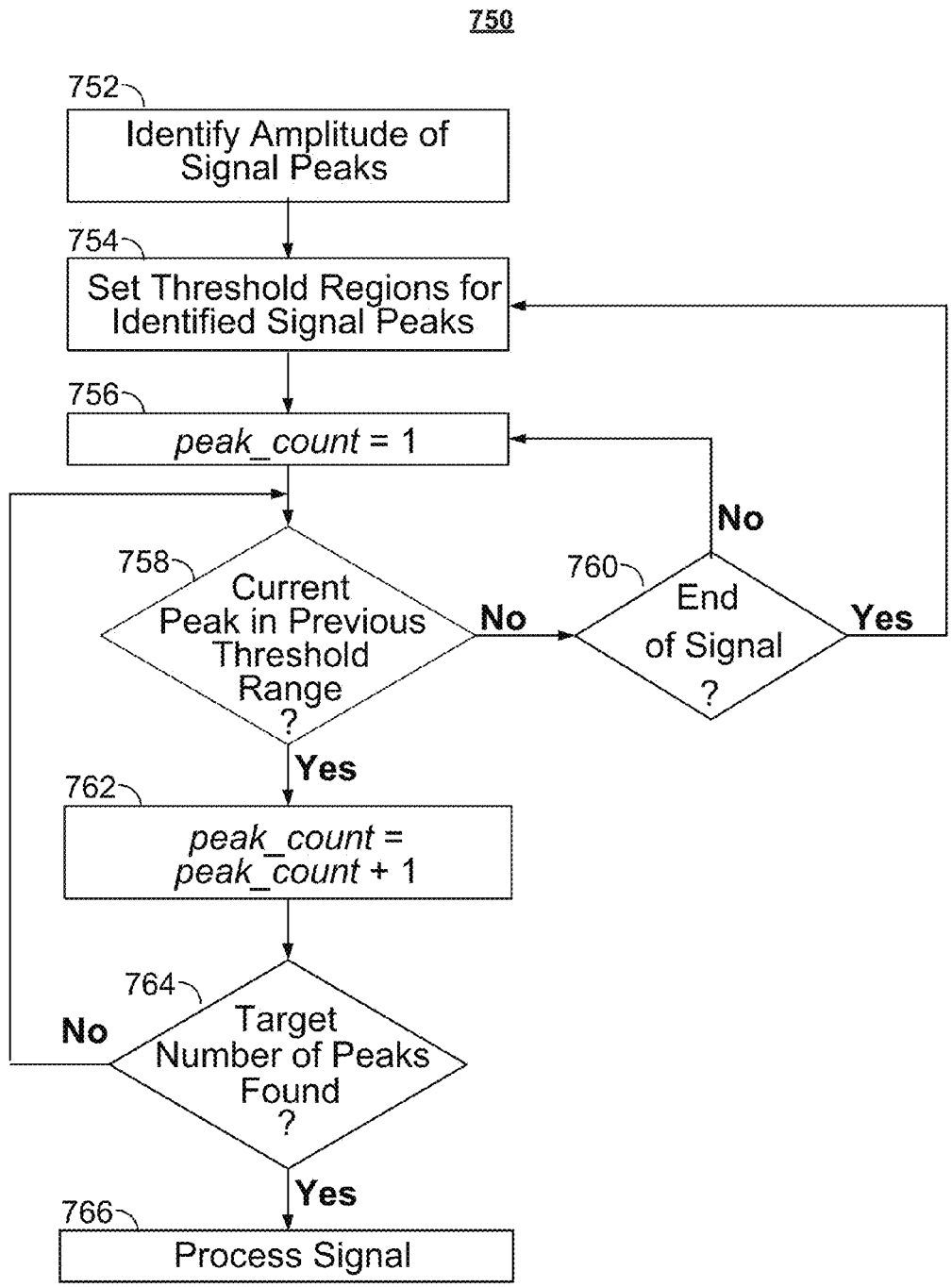
Figure 7D:
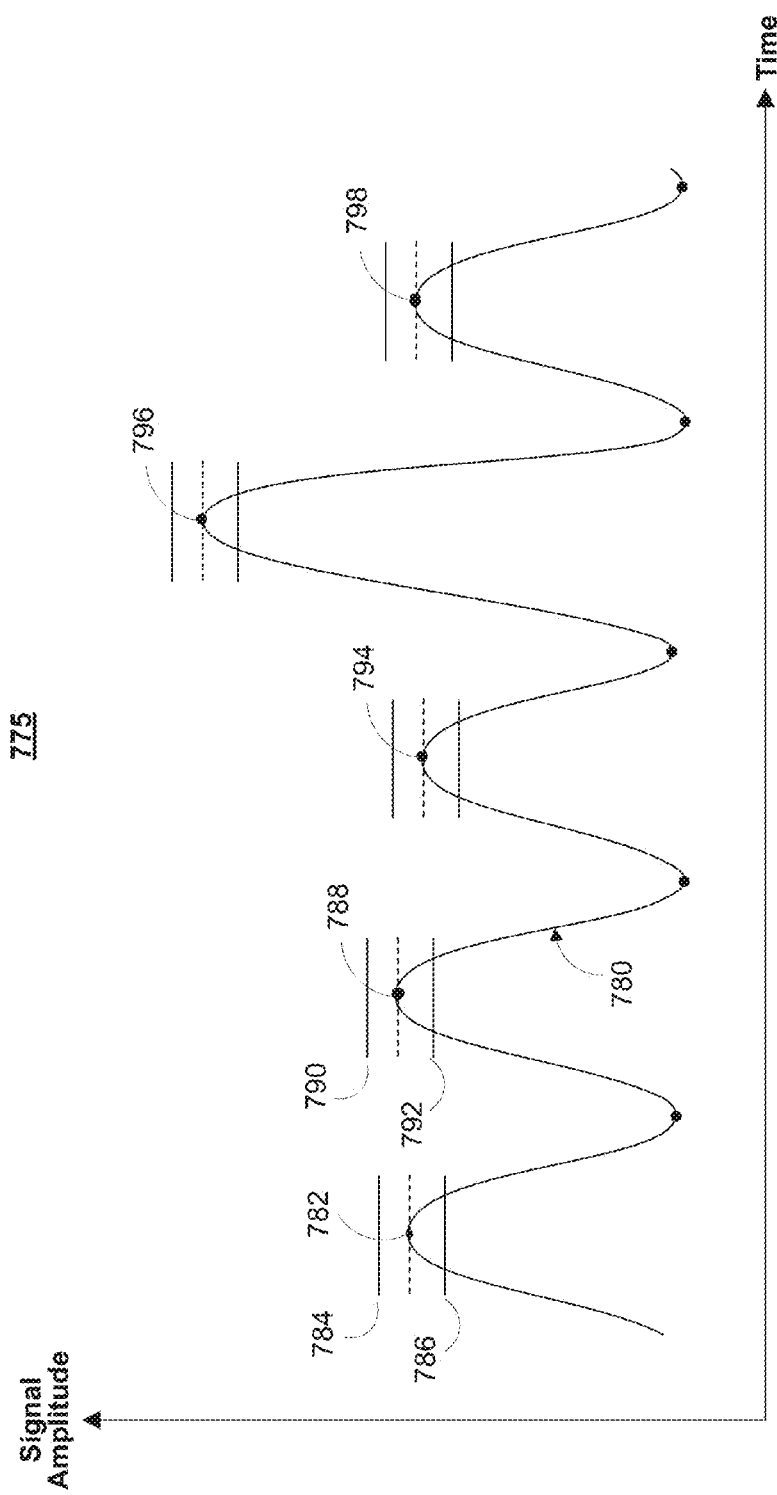
FIG. 7D is an illustrative plot of a PPG signal that may be processed using the techniques shown in FIG. 7C in accordance with an embodiment.

FIG. 7C depicts another illustrative process for selecting a consistent part of a signal, e.g., PPG signal 505 (FIG. 5) or 780 (FIG. 7D). Process 750 may select a consistent part of a signal by analyzing the amplitudes of signal peaks. Process 750 may correspond to a further embodiment of process 600, and more particularly, may correspond to a further embodiment of step 650 of FIG. 6. Process 750 may operate according to an amplitude-based consistency metric that specifies a separate upper and lower threshold for each signal peak of an obtained signal, e.g. PPG signal 780 (FIG. 7D) and that determines if a target number of consecutive valid signal peaks are present in the obtained signal. In an embodiment of process 750, a signal peak may be determined to be valid if the amplitude of the signal peak lies within a threshold region corresponding to a previous signal peak, as will be illustrated below in relation to plot 775 (FIG. 7D). Process 750 may be referred to as a consistency in amplitude technique.

Process 750 may start at step 752. At step 752, the amplitude values of all the signal peaks of the obtained signal may be identified. For example, at step 752, process 750 may search the signal obtained by process 600 (FIG. 6) at step 620 (FIG. 6), and/or that may have been generated by a signal generator such as signal generator 410 (FIG. 4). The amplitude values of the signal peaks may be determined using a method similar or identical to the signal processing methods described in relation to step 640 (FIG. 6). For example, process 750 may obtain PPG signal 780 (FIG. 7D) at step 752, and may identify signal peak amplitude values 782, 788, 794, 796, and 798 (all of FIG. 7D). Process 750 may identify signal peak amplitude values, for example, using microprocessor 48 (FIG. 2) or processor 412 (FIG. 4).

At step 754, process 750 may set threshold regions for each signal peak identified at step 752 (i.e., process 750 may set threshold regions on a peak-by-peak basis). For example, process 750 may obtain PPG signal 780 (FIG. 7D) and may set the threshold region defined by amplitude values 784 and 786 for signal peak 782 (all three of FIG. 7D), threshold region defined by amplitude values 790 and 792 for signal peak 788 (all three of FIG. 7D), and may similarly set individual threshold regions for signal peaks 794, 796, and 798 (all of FIG. 7D). Thus, the threshold regions set at step 754 may be time-varying.

Process 750 may then identify the number of consecutive signal peaks for which each signal peak amplitude value is within the threshold region of the previous signal peak. In an embodiment, process 750 may implement this peak-counting technique as follows. At step 756, process 750 may set a counter peak_count equal to the value one, where peak_count represents the number of consecutively identified valid signal peak amplitude values. At step 758, process 750 may determine if a current signal peak lies within the threshold range corresponding to a previous signal peak. For example, if the current signal peak is signal peak 788 (FIG. 7D), process 750 may determine if signal peak 788 (FIG. 7D) lies within the threshold range specified by amplitude values 784 and 786 (both of FIG. 7D). Alternatively, if the current signal peak is signal peak 794 (FIG. 7D), then process 750 may determine if signal peak 794 (FIG. 7D) lies within the threshold range specified by amplitude values 790 and 792 (both of FIG. 7D).

If the current signal peak is determined to lie within the previous threshold range at step 758, process 750 may continue to step 762, where the value of peak_count may be incremented (i.e., signifying that the current peak has been identified to be a valid signal peak). Process 750 may then continue to step 764, where process 750 may determine if a target number of consecutive signal peaks have been identified or found (e.g., by comparing the value of peak_count to a specified threshold). If the target number of signal peaks have been found, process 750 may continue to step 766, where process 750 may process the signal by, e.g., normalizing the portion of the signal corresponding to the signal peaks (i.e., the consistent part of the signal). For example, process 750 may filter the signal corresponding to the signal peaks to normalize signal peak values, remove noise-artifacts, and/or perform curve smoothing and interpolation operations. In alternative embodiment of process 750, if the target number of signal peaks are not found at step 764, process 750 may instead return to step 758 and continue to identify value signal peaks (rather than continue to step 766). If at step 764, it is determined that the target number of consecutive signal peaks have not been identified, process 750 may return to step 758, and continue to test signal peaks.

If, at step 758, the current signal peak is determined not to fall within the threshold region of the previous signal peak, then process 750 may continue to step 760. At step 760, process 750 may test the signal obtained, e.g., at step 620 of process 600 (both of FIG. 6). If there are sufficiently more signal peaks remaining in the obtained signal to test, process 750 may set peak_count equal to the value one at step 756 (thereby resetting the count of the consecutive valid signal peaks found). Process 750 may then proceed to identify a new set of signal peaks according to FIG. 7C. If, at step 760, it is determined that there is not a sufficient number of new signal peaks to test, then process 750 may return to step 754 and increase the width of one or more of the signal peak threshold regions. For example, at step 754, process 750 may change amplitude values 784 and 786 corresponding to signal peak 782 (all of FIG. 7D) and/or the threshold region defined by amplitude values 790 and 792 corresponding to signal peak 788 (all of FIG. 7D) to increase the threshold regions of signal peak 782 and 788 (both of FIG. 7D), respectively. Process 750 may similarly increase the threshold regions corresponding to signal peaks 794, 796, and 798 (all of FIG. 7D). In general, process 750 may set the width of the threshold regions corresponding to signal peaks of the obtained signal, for example, signal peaks 782, 788, 794, 796, and 798 of FIG. 7D according to any suitable criteria or criterion. One or more of these threshold regions may be set so that each threshold region has a constant width, so that the width of the threshold region depends on the corresponding signal peak amplitude value (e.g., the width of the threshold region corresponding to signal amplitude values 790 and 792 of FIG. 7D may be set as a percentage of the amplitude value of signal peak 788 of FIG. 7D, for example plus or minus 10-percent of the signal peak amplitude value) or according to some other linear or non-linear function of the signal peak amplitude value. By setting threshold regions in this manner, process 750 may account for slowly time-varying signals.

FIG. 8 depicts an illustrative process for selecting a consistent part (or parts) of a signal, e.g., PPG signal 505 (FIG. 5), by analyzing the periods between signal peaks (these periods will also referred to as interpeak distances and/or interpeak periods) in accordance with some embodiments. Process 800 may correspond to a further embodiment of process 600, and/or may correspond to a further embodiment of step 650 of FIG. 6. Process 800 may be used to remove the effects of biological phenomena from a signal, such as PPG signal 505 (FIG. 5), prior to further analysis of the signal. Process 800 may be used to remove, e.g., the effects of erroneous beats, include those caused by an ectopic heart beat, or movement by a patient such as patient 40 (FIG. 2). For example, process 800 may be applied to a signal similar or identical to PPG signal 505 (FIG. 5), and may be used calculate and analyze the interpeak distances of the signal, for example, interpeak distances 530, 532, 534, and 536 (all of FIG. 5). Process 800 may operate according to interpeak-based consistency metric that specifies a target number of interpeak distance segments (e.g., three interpeak distance segments), the interpeak distance segments being solely or jointly suitable in some sense (e.g., mean interpeak distance). Process 800 may sequentially calculate interpeak distances from a signal, for example, using a processor such as processor 412 (FIG. 4) or microprocesor 48 (FIG. 2), to remove or modify sections of the signal that have undesirable interpeak distances. Process 800 may be referred to as a consistency in period technique.

Process 800 may start at step 810, where a first interpeak distance of a signal is calculated. For example, step 810 may determine interpeak distances of a signal obtained by process 600 (FIG. 6) at step 620 (FIG. 6), and/or that may have been generated by a signal generator such as signal generator 410 (FIG. 4). The location of the first two signals peaks of a signal may be determined, e.g., using a method similar or identical to the signal processing methods described in relation to step 640 (FIG. 6). Process 800 may then determine a first interpeak distance by computing the time-distance between the first two signal peaks. The first two signal peaks may correspond to the first two signal peaks in time, e.g., signal peaks 510 and 512 of PPG signal 505 (FIG. 5), or it may correspond to the first two consecutive signal peaks found through a suitable signal processing algorithm, such as an extrema-finding algorithm.

Process 800 may continue at step 820, where the determined interpeak distance is compared to a criterion, e.g., a length-threshold, a variance metric, and/or an average signal power metric. Additionally, the criterion may depend on previous and/or future values of the interpeak distances determined, e.g., at step 810 during previous iterations of process 800. Thresholds and other parameters used to calculate the criterion at step 820 may be based on analytic results, on experimental data, and/or may be determined heuristically. For example, these thresholds and parameters may be set by, e.g., using user inputs 56 (FIG. 2). Various criteria may be considered in combination at step 820 to improve the accuracy of the analysis.

At step 830, a decision may be made regarding the suitability of the interpeak distance determined at step 810. The decision may be made by comparing the interpeak distance determined at step 810 to a threshold determined at step 820. Further, an interpeak distance (e.g., interpeak distance 534 of FIG. 5) may be determined or otherwise influenced by the suitability of previous and/or subsequent interpeak distances. If, at step 830, the interpeak distance is determined not to be suitable, process 800 may continue to step 860, where the portion of the signal corresponding to the unsuitable interpeak distance may be removed, spliced, transformed, or otherwise modified. Further, at step 860, process 800 may concatenate the remaining portion of the signal so that the resultant signal is continuous in time. Process 800 may then continue to step 870.

If, at step 830, the interpeak distance is determined to be suitable, process 800 may continue to step 840. At step 840, process 800 may determine if a target or predetermined number of interpeak periods have been found through consecutive iterations of process 800. For example, process 800 may operate on PPG signal 505 (FIG. 5), and/or may specify a target number of three (or any other suitable number) interpeak periods. The target number of interpeak periods may depend, e.g., on the expected duration of the signal needed for further analysis. If the target number of interpeak periods has been determined, process 800 may continue to step 850. At step 850, process 800 may further operate on or normalize the portion of the signal corresponding to the determined interpeak periods (i.e., the consistent parts of the signal). For example, process 800 may filter the portion of the signal corresponding to the interpeak periods to normalize signal values, remove noise-artifacts, and/or use perform curve smoothing and interpolation operations. If the target number of interpeak distances have not yet been found at step 840, process 800 may continue to step 870.

At step 870, process 800 may continue to determine and analyze interpeak periods by identifying a next interpeak period. For example, if the last identified interpeak period (identified either at step 810 or at a previous iteration of step 870) was, e.g., interpeak period 532 (FIG. 5), then process 800 may identify interpeak period 534 (FIG. 5) as the next interpeak period at step 870. Process 800 may continue in this manner until it is determined, e.g., at step 840, that the target number of interpeak periods has been identified.

The criteria and metrics described, e.g., at step 650 (FIG. 6) and step 830 are illustrative, and many other criteria and metric may be used in other embodiments. Probabilistic criteria and/or metrics may be used, e.g., in which the numerically or analytically determined probability that a portion of a signal is suitable is determined, and/or adaptive filtering techniques may be used to determine the suitability of a signal obtained in pulse oximetry system 10 (FIG. 1), or any other valid system. Further, multiple metrics may be used, jointly or in combination, to find an overall region of maximum consistency in the signal tested, e.g., at step 650 (FIG. 6). The calculations described relative in FIGS. 6-8 may be processed using a processor such as processor 412 (FIG. 2) or microprocessor 48 (FIG. 2), and data related to the consistency metrics may be stored, e.g., in ROM 52 (FIG. 2), and/or RAM 54 (FIG. 2). The described consistency in period techniques in process 800 may be used in conjunction with a PPG signal and/or a filtered or transformed version of a PPG signal to determine, e.g., the respiration rate of patient 40 (FIG. 2).

Consistency in amplitude techniques (described for example, in FIGS. 7A and 7B) and consistency in period techniques (described, for example, in FIG. 8) are illustrative of a variety of techniques for determining the consistent regions of a signal trace (such as the signal trace shown in FIG. 5). These techniques, as well as others, may be used in combination to effectively determine the consistency of a portion of a signal obtained in pulse oximetry system 10 (FIG. 1), or any other suitable system.

The techniques described above (e.g., in FIGS. 6-8) identify and process signal peaks to determine signal consistency (e.g., step 640 (FIG. 6), step 702 (FIG. 7A), step 727 (FIG. 7B), and step 810 (FIG. 8)). However, in an alternative embodiment, any other suitable characteristic (or characteristic set of points) of a signal may be used. For example, the troughs of a signal obtained in pulse oximetry system 10 (FIG. 1) may be used, or a position corresponding to the same relative phase may be used. Alternatively or additionally, localized phase information or other characteristics may be derived from a wavelet transform of a signal and used to determine signal consistency.

Figure 9:
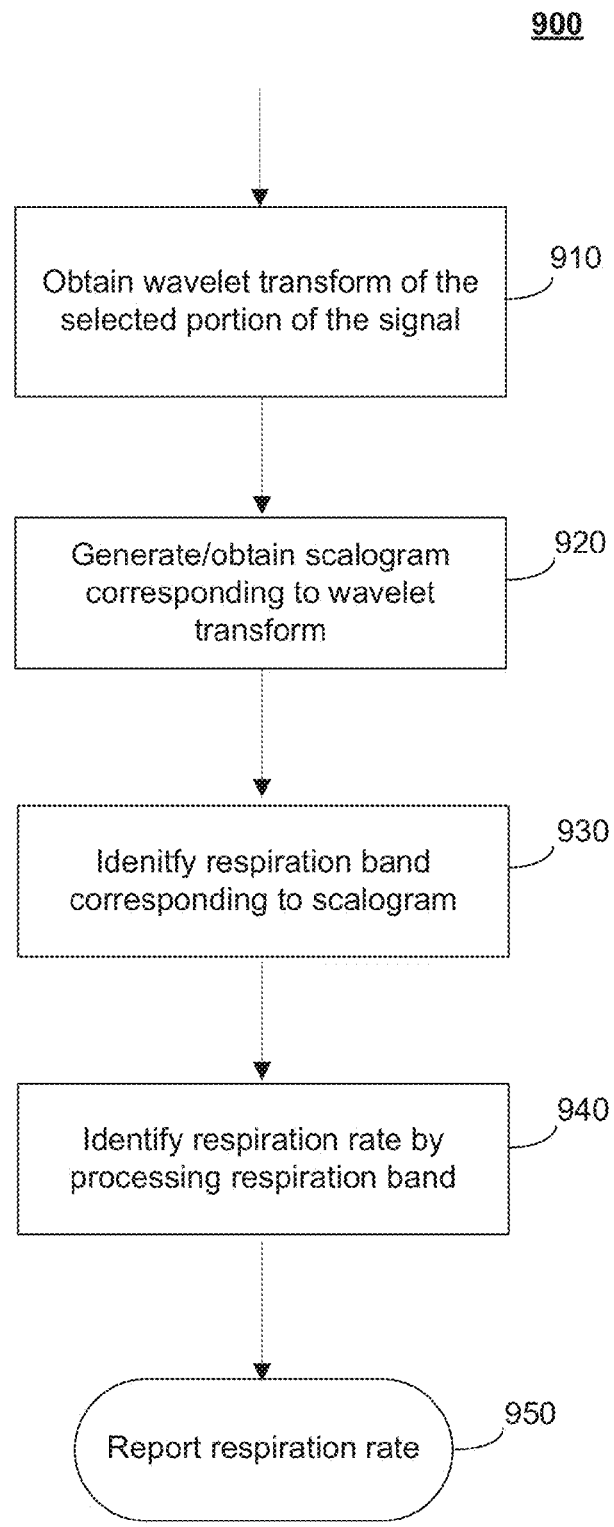
FIG. 9 depicts an illustrative process for analyzing a selected portion of a signal, e.g., a consistent portion of a PPG signal, to determine a rate of occurrence of a biological parameter.

FIG. 9 depicts an illustrative process for analyzing a selected portion of a signal, e.g., a consistent portion of a PPG signal, to determine a rate of occurrence of a parameter. For example, process 900 may be used to determine or estimate the respiration rate of patient such as patient 40 (FIG. 2). Process 900 may correspond to a further embodiment of step 670 of process 600.

At step 910, the wavelet transform of a signal may be obtained. Such a wavelet transform may be obtained, for example, by system 10 (FIGS. 1 and 2) or system 400 (FIG. 4). At step 920, the scalogram of the wavelet transform may be generated or otherwise obtained using, for example a processor such as processor 412 (FIG. 4) or microprocessor 48 (FIG. 2). In addition to the scalogram, other parts of the wavelet transform may be determined at step 920. For example, the transform modulus, phase, real, and/or imaginary parts may be generated at step 920 in addition to the scalogram. Each of these features may then be used, either individually or in combination, in the subsequent steps of process 900 to determine the respiration rate of a patient.

At step 930, the respiration band of a scalogram may be identified based on one or more characteristics of the scalogram obtained in step 920. The respiration band of the scalogram may generally reflect the breathing pattern of a patient, e.g., patient 40 (FIG. 2). The respiration band of the scalogram obtained in step 920 may be identified using characteristics of the scalogram including the energy and structure of the scalogram, and the signal-to-noise levels in various regions of scalogram. In one embodiment, this information may be calculated one or more times using different time-window sizes. The number and type of time-window sizes that are used may depend on the anticipated respiration rate, the available computational resources (e.g., the amount of ROM 52 (FIG. 2) and/or RAM 54 (FIG. 2) and the speed of processor 412 (FIG. 4) and/or microprocessor 48 (FIG. 2)), as well as on possible input derived from user inputs 56 (FIG. 2).

At step 940, the scalogram characteristics determined in step 930 corresponding to the respiration band may be analyzed. Analyzing the characteristics may generally involve parsing, combining, and/or weighing results obtained in previous steps of process 900 to obtain a single, overall estimate of the respiration rate. Step 940 may incorporate the use of past scalogram data that has been obtained in previous iterations of process 900 to determine a respiration rate. The respiration rate may be represented by a number from 1 to 100, where a larger number indicates a larger respiration rate (any other suitable number range could be used instead). Step 940 may also involve the parameterization and/or curve fitting of data obtained in steps 920 and 930 using, for example, linear least-squares fitting of data or any other suitable interpolation technique. Such parameterization and/or curve fitting may be performed, for example, by processor 412 (FIG. 4) or microprocessor 48 (FIG. 2), and may additionally depend on parameters entered by a user through user inputs 56 (FIG. 2). To estimate a respiration rate at step 940, process 900 may use, for example, maximum-likelihood techniques to combine data when the prior probability of a given respiration rate is known, and Neyman-Pearson combining techniques may be used when the prior probability of a given respiration rate is unknown.

At step 950, the respiration rate determined or estimated at step 940 may be reported. For example, the respiration rate may be reported by generating an audible alert or, for example, using speaker 22 (FIG. 2) as well as possibly through other audio devices, generating an on-screen message, for example, on display 20 (FIG. 1) or display 28 (FIG. 1), generating a pager message, a text message, or a telephone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration medicine, for example, which is controlled in part or fully through a system such as system 10 (FIG. 1).

It will also be understood that the above method may be implemented using any human-readable or machine-readable instructions on any suitable system or apparatus, such as those described herein.

The foregoing is merely illustrative of the principles of this disclosure and various modifications may be made by those skilled in the art without departing from the scope and spirit of the disclosure. The following claims may also describe various aspects of this disclosure.

What is claimed is:

1. A method for processing a physiological signal, comprising:
    obtaining a photoplethysmograph (PPG) signal from a pulse oximetry sensor;
    selecting, using a pulse oximeter, a current portion of the PPG signal for analysis;
    identifying, using the pulse oximeter, a plurality of signal peaks in the current portion of the PPG signal;
    determining, using the pulse oximeter, a peak characteristic for each of the plurality of signal peaks, wherein the peak characteristic comprises one or more of peak amplitude, trough amplitude, and interpeak distance;

comparing, using the pulse oximeter, the peak characteristic for each of the plurality of signal peaks to each other to determine if the current portion of the PPG signal is consistent; and responsive to determining that the current portion of the PPG signal comprising a plurality of peaks is consistent, determining, using the pulse oximeter, respiration rate based at least in part on the current portion of the PPG signal.

2. The method of claim 1, wherein the peak characteristic comprises peak amplitude and wherein comparing the peak characteristic for each of the plurality of signal peaks comprises:

selecting a first signal peak from the plurality of signal peaks; and setting a lower threshold at an amplitude level smaller than the determined peak amplitude associated with the first signal peak, and setting an upper threshold at an amplitude level larger than the determined peak amplitude associated with the first signal peak.

3. The method of claim 2, wherein comparing the peak characteristic for each of the plurality of signal peaks further comprises:

selecting a second signal peak from the plurality of signal peaks;

determining if the determined peak amplitude associated with the second signal peak is generally greater than the lower threshold; and determining if the determined peak amplitude associated with the second signal peak is generally lower than the upper threshold.

4. The method of claim 1, wherein the peak characteristic comprises interpeak distance.

5. The method of claim 4, wherein comparing the peak characteristic for each of the plurality of signal peaks comprises:

determining if a first interpeak distance exceeds a threshold value; and if the first interpeak distance exceeds the threshold value, determining if the first interpeak distance exceeds one or more past or future interpeak distances.

6. The method of claim 1, wherein if a current portion of the PPG is determined not to be consistent, the current portion of the PPG signal is removed from a processed version of the PPG signal.

7. The method of claim 1, wherein obtaining the PPG signal from the pulse oximetry sensor further comprises processing the PPG signal to remove artifacts present in the PPG signal.

8. The method of claim 1, wherein the plurality of signal peaks are identified using an extrema-finding process.

9. A system for processing a physiological signal, the system comprising:

a pulse oximeter configured for:
obtaining a photoplethysmograph (PPG) signal from a pulse oximetry sensor;
selecting a current portion of the PPG signal for analysis;
identifying a plurality of signal peaks in the current portion of the PPG signal;
determining a peak characteristic for each of the plurality of signal peaks, wherein the peak characteristic comprises one or more of peak amplitude, trough amplitude, and interpeak distance comparing the peak characteristic for each of the plurality of signal peaks to each other to determine if the current portion of the PPG signal is consistent; and responsive to determining that the current portion of the PPG signal comprising a plurality of peaks is consistent, determining respiration rate based at least in part on the current portion of the PPG signal.

10. The system of claim 9, wherein the peak characteristic comprises peak amplitude and wherein the pulse oximeter is further configured for comparing the peak characteristic for each of the plurality of signal peaks at least in part by:

selecting a first signal peak from the plurality of signal peaks; and setting a lower threshold at an amplitude level smaller than the determined peak amplitude associated with the first signal peak, and setting an upper threshold at an amplitude level larger than the determined peak amplitude associated with the first signal peak.

11. The system of claim 10, wherein the pulse oximeter is further configured for comparing the peak characteristic for each of the plurality of signal peaks at least in part by:

selecting a second signal peak from the plurality of signal peaks;

determining if the determined peak amplitude associated with the second signal peak is generally greater than the lower threshold; and determining if the determined peak amplitude associated with the second signal peak is generally lower than the upper threshold.

12. The system of claim 9, wherein the peak characteristic comprises interpeak distance.

13. The system of claim 12, wherein the pulse oximeter is further configured for comparing the peak characteristic for each of the plurality of signal peaks at least in part by:

determining if a first interpeak distance exceeds a threshold value; and if the first interpeak distance exceeds the threshold value, determining if the first interpeak distance exceeds one or more past or future interpeak distances.

14. The system of claim 9, wherein if a current portion of the PPG is determined not to be consistent, the current portion of the PPG signal is removed from a processed version of the PPG signal.

15. The system of claim 9, wherein obtaining the PPG signal from the pulse oximetry sensor further comprises processing the PPG signal to remove artifacts present in the PPG signal.

16. The system of claim 9, wherein the plurality of signal peaks are identified using an extrema-finding process.

17. A non-transitory computer readable medium comprising:

computer program instructions stored therein for causing a pulse oximeter to:
obtain a photoplethysmograph (PPG) signal from a pulse oximetry sensor;
select a current portion of the PPG signal for analysis;
identify a plurality of signal peaks in the current portion of the PPG signal;
determine a peak characteristic for each of the plurality of signal peaks, wherein the peak characteristic comprises one or more of peak amplitude, trough amplitude, and interpeak distance
compare the peak characteristic for each of the plurality of signal peaks to each other to determine if the current portion of the PPG signal is consistent; and
responsive to determining that the current portion of the PPG signal comprising a plurality of peaks is consistent determining respiration rate based at least in part on the current portion of the PPG signal.

18. The computer readable medium of claim 17, wherein the peak characteristic comprises peak amplitude and wherein the computer program instructions cause the pulse oximeter to compare the peak characteristic for each of the plurality of signal peaks by:

selecting a first signal peak from the plurality of signal peaks; and setting a lower threshold at an amplitude level smaller than the identified amplitude level associated with the first signal peak, and setting an upper threshold at an amplitude level larger than the identified amplitude level associated with the first signal peak.

* * * * *